(12) United States Patent
Taleyarkhan

(10) Patent No.: US 10,281,598 B2
(45) Date of Patent: May 7, 2019

(54) COMPOSITIONS AND METHODS FOR MONITORING ACTINIDES

(71) Applicant: Purdue Research Foundation, West Lafayette, IN (US)

(72) Inventor: Rusi Taleyarkhan, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 491 days.

(21) Appl. No.: 14/777,307

(22) PCT Filed: Mar. 14, 2014

(86) PCT No.: PCT/US2014/028474
§ 371 (c)(1),
(2) Date: Sep. 15, 2015

(87) PCT Pub. No.: WO2014/144176
PCT Pub. Date: Sep. 18, 2014

(65) Prior Publication Data
US 2016/0025872 A1    Jan. 28, 2016

Related U.S. Application Data

(60) Provisional application No. 61/791,657, filed on Mar. 15, 2013.

(51) Int. Cl.
*G01N 23/00* (2006.01)
*G01N 1/00* (2006.01)
(Continued)

(52) U.S. Cl.
CPC .................. *G01T 5/06* (2013.01); *G01N 1/00* (2013.01); *G01N 23/00* (2013.01); *G01T 3/00* (2013.01); *G01T 3/008* (2013.01)

(58) Field of Classification Search
CPC ... G01T 3/00; G01T 5/00; G01N 1/00; G01N 23/00
(Continued)

(56) References Cited

U.S. PATENT DOCUMENTS

2009/0296871 A1* 12/2009 Taleyarkhan ........... G01T 1/167
376/153
2011/0174990 A1    7/2011 Taleyarkhan
2014/0117246 A1*  5/2014 Zhou ...................... G01T 1/185
250/375

OTHER PUBLICATIONS

Lapinskas et al. ("Tension metastable fluid detection systems for special nuclear material detection and monitoring", Nuclear Engineering and Design, 240, pp. 2866-2871, 2010).*
(Continued)

*Primary Examiner* — David P Porta
*Assistant Examiner* — Meenakshi Sahu
(74) *Attorney, Agent, or Firm* — Purdue Research Foundation; Zhigang Rao

(57) ABSTRACT

Compositions and methods for monitoring the quantity of actinides present in a test sample are disclosed. Compositions and methods for monitoring the motion of special nuclear materials through space are also described. Compositions and methods for monitoring the quantity of a fissile special nuclear material present in a test sample are disclosed. Compositions and methods for monitoring actinides during reprocessing of spent nuclear fuel after 30-year cool down are disclosed. Compositions and methods for monitoring actinides during reprocessing of spent nuclear fuel after 180 day cool down are also disclosed.

2 Claims, 13 Drawing Sheets

(51) Int. Cl.
  *G01T 3/00* (2006.01)
  *G01T 5/06* (2006.01)
(58) Field of Classification Search
  USPC .................................................. 250/390.04
  See application file for complete search history.

(56) References Cited

OTHER PUBLICATIONS

Lapinskas J., Tension metastable fluid detection systems for special nuclear material detection and monitoring, Nuclear Engineering and Design 240 (2010) 2866-2871.
Lapinskas J., Tension metastable fluid nuclear particle Detector—Qualification and comparisons, Nuclear Engineering and Design 239 (2009) 2152-2159.
Jeffery A., et al., Tensioned Metastable Fluid Detectors in Nuclear Security for Active Interrogation of Special Nuclear Materials—Part B, World Journal of Nuclear Science and Technology, 2011, 1, 66-76.

* cited by examiner

Uranium: 4.2MeV - 4.8MeV, Pu-239: 5.2 MeV, and Pu-238: 5.6 MeV

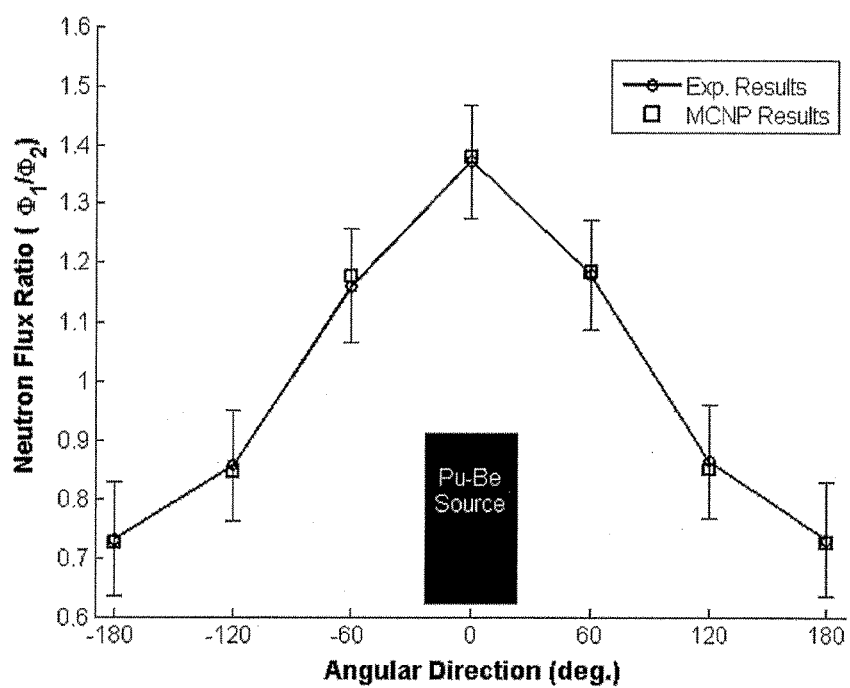
FIG 5. Confirmation of ability to detect the source direction for neutron emissions [Archambault, 2011].

FIG. 6
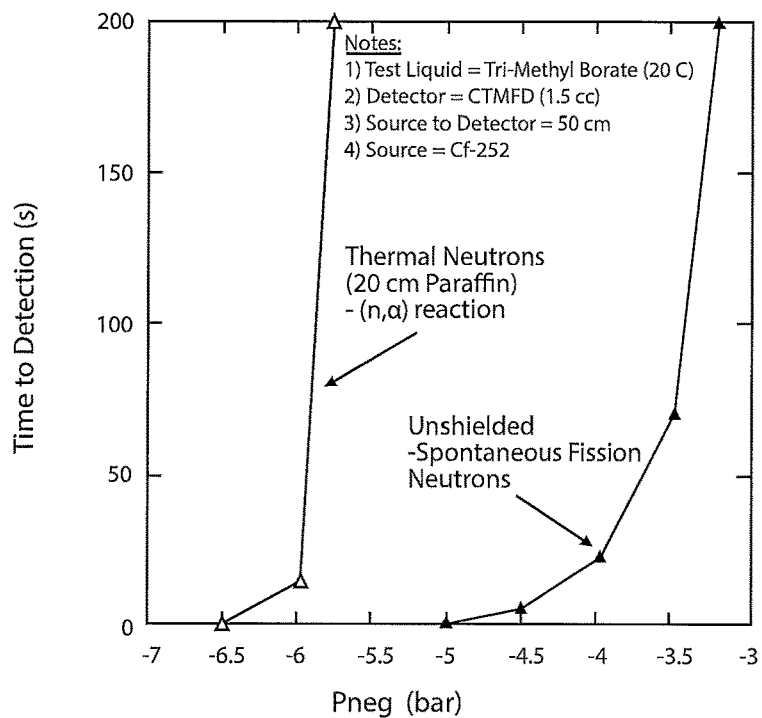
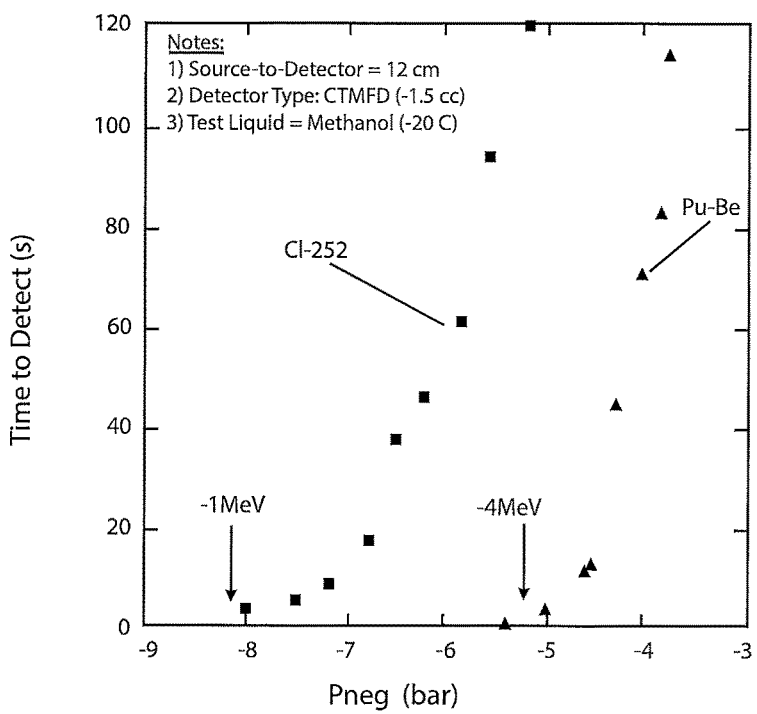

FIG. 10
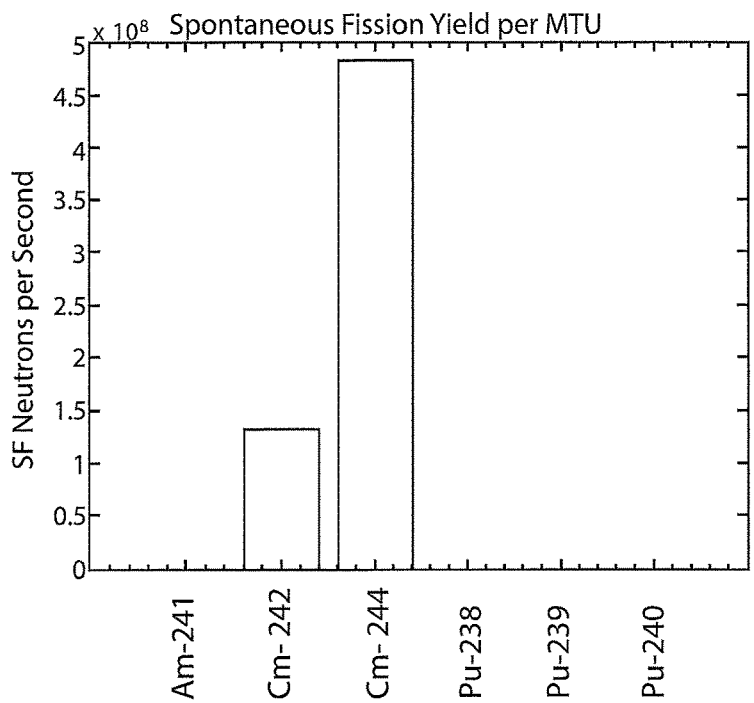
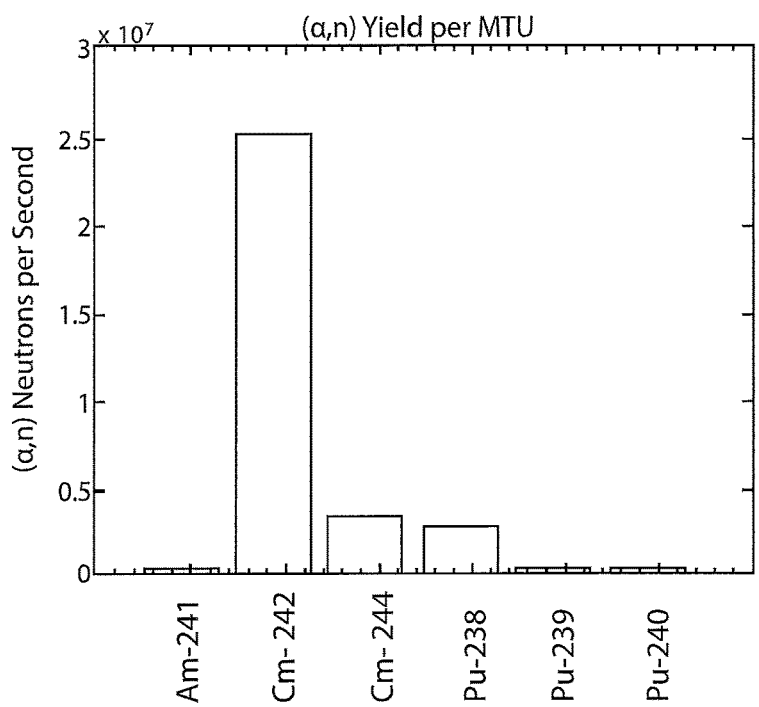

COMPOSITIONS AND METHODS FOR MONITORING ACTINIDES

GOVERNMENT RIGHTS

This invention was made with government support under DE-FG07-07ID14890 awarded by the Department of Energy (DOE). The United States government has certain rights in the invention.

BACKGROUND OF INVENTION

The U.S. Department of Energy has developed methods for reprocessing spent nuclear fuel in commercial reprocessing plants. These methods present challenges within the nuclear industry with regard to security. The majority of this development was accomplished under the Advanced Fuel Cycle Initiative, building on the legacy of process research and development over the past 50 years. The emergence of the new Global Nuclear Energy Partnership aims to continue and expand the development of Advanced Fuel Cycle Initiative processing methods. This initiative has elevated the U.S. and worldwide commitment to advance fuel processing. These advanced processing methods need to be scaled up and engineered for real-scale implementation.

The most prominent processing method under development is named UREX+ depicted schematically in FIG. 1. The name actually refers to a family of processing methods that begins with the Uranium Extraction (UREX) process and incorporates a variety of other methods to separate uranium, selected fission products, and the transuranic isotopes from dissolved Spent Nuclear Fuel. UREX+ is similar to the well-known PuREX process currently used worldwide (e.g., Sellafield, Great Britain; La Hague in France; and Rokasho in Japan). The similarities derive from multiple chemical separation processes that are used to remove the major sources of radioactivity with specific goals to recycle U and Pu into the fuel cycle.

Processing will be needed for over 1,000 tons of fuel per day in the future to accommodate the worldwide Spent Nuclear Fuel from about 1,000 operating reactors each with an inventory of about 100 T of $UO_2$ and, additionally for the reprocessing of the legacy inventory of Spent Nuclear Fuel. As Global Nuclear Energy Partnership and the U.S. Department of Energy moves toward implementation of UREX+ over the next 20 years, strategies, material controls, and accountability methods will be required. Monitoring actinides with higher molecular weight during aqueous separations is a critical research area of the U.S. Global Nuclear Energy Partnership and Advanced Fuel Cycle Initiative programs. A key aspect of monitoring for material accountability is a method for assessing in real-time composition of the Spent Nuclear Fuel in order to detect possible diversion of Transuranic elements such as Pu. Such timely detection is especially important for $^{239}Pu$. A single fuel assembly can contain close to 7 kg, the quantity which is sufficient to produce Nagasaki-type nuclear explosives. Likewise, in the Material Balance Areas of critical nuclear installations (e.g., weapons plants), the tracking and inventory control is crucial for safeguarding and securing relevant nuclear materials. By providing an on-line material accounting system during the recycling processes, uninvited diversion of the material streams may be curbed. Currently, however, maintenance and control of such Special Nuclear Materials (SNMs) are conducted via time-consuming off-site monitoring and assessments, which significantly reduce the speed and efficacy of reprocessing and functioning of critical nuclear facilities.

Currently, alpha emitter detection requires time-consuming off-site laboratory based methods, and most on-line neutron detection systems are readily saturated in the extreme beta-gamma fields associated with the copious quantities of fission products like $^{137}Cs$. As noted in FIG. 1, the first step in reprocessing at any reprocessing facility is to chop the Spent Nuclear Fuel (SNF) and dissolve the materials, known as accountable materials, in an acidic solution, which is accountable for the entirety of nuclear materials in the SNF. The accountable materials containing solution is then transferred to an accountability tank. Samples are taken and measurements are made to crudely determine the total quantity of initial nuclear material inventory. Determining the initial Special Nuclear Materials quantity is crucial in maintaining material accountability throughout the process and in identifying whether diversion, if any, has occurred.

Unfortunately, Near Real Time Accountability of transuranic actinides has not been achieved up until now. Near real time refers to the rate of detection of the relevant quantities of nuclear materials during the various stages of the SNF reprocessing in the span of a few hours, which is generally commensurate with the rate at which the SNF is reprocessed. While techniques for measuring near real time in bulk quantities, e.g., the volume of dissolved fuel and flow rates have been developed, Near Real Time Accountability related to on-line measurement of the elemental and isotopic concentrations was not possible with conventional detection methods (e.g., with K-Edge densitometry; X-ray fluorescence; Hybrid K-Edge/X-ray fluorescence densitometry; mass spectrometry; high resolution gamma spectrometry; isotope dilution gamma spectroscopy; constant coulomb coulometry; titrimetry; gravimetry; spectrophometry; calorimetry). In general, current methods do not offer Near Real Time Accountability capability for isotopic assessments, but rather require off-site shipment to special laboratories for relevant quantities data which may take from a few days to weeks. More importantly, current methods do not provide the means to determine Special Nuclear Materials isotopic inventories in-situ.

A detection system and methodology that permits on-line assessment of the U and Pu type actinides at the earliest stages (and subsequent stages), and that is complemented with current technology (e.g., simple methods of measuring weight and volume) for later stages would provide major improvement to reprocessing both in operational efficacy and in safety. A framework and methodology that achieves this goal by using a Tension Metastable Fluid Detector (TMFD) sensor system is described.

Spent Nuclear Fuel from a typical light water reactor contains a large collection of fission products with isotopes that span the periodic table from $^{72}Fe$ to $^{167}Er$ (plus a minor amount of tritium from tertiary fissions). In addition, Spent Nuclear Fuel contains radioactive activation products and transuranic actinide elements (i.e., Pu, Np, Am and Cm). While the majority of the fission products are gamma-beta emitters, it is the alpha-emitting uranium and transuranic isotopes that cause significant security as well as health safety concerns. Table 1 depicts the inventory of uranium and transuranic elements in representative spent fuel assemblies from a pressurized water reactor. All of the uranium and transuranic isotopes emit alpha particles but only some of them generate also significant quantities of neutrons from spontaneous fission.

The data in Table 1 illustrate both common grounds and differences between U and Pu isotopes in Spent Nuclear Fuel. The commonality is that both isotope groups exhibit alpha particle emissions with energies defined by the individual isotopes that vary between about 4 MeV to about 6 MeV. The differences arise in neutron emissions due to spontaneous fission. Uranium has a maximum emission rate in Table 1 of about $10^4$ n/s/MTU for $^{238}$U. Such value, when diluted and spread out over space in piping (e.g., to over 1 $m^2$ of surface area), may be difficult to passively measure over cosmic background neutron fluxes. On the other hand, some of the transuranic isotopes like $^{244}$Cm can emit about $10^9$ n/s/MTU. Such emission constitutes a readily measurable quantity (diluted or otherwise), using Tension Metastable Fluid Detector technology even in extreme gamma-beta fields wherein conventional sensors are saturated.

TABLE 1

Composition of a typical SNF assembly from a 2000 $MW_t$ PWR. (Takahama-3, Initial U-235 enrichment: 4.11%, Burn-up: 47.03 GWd/mtu, Cooling time: 0 y)

| Isotope | Mass (kg · MTU) | Half Life (years) | Alpha Ratio (%) | Alpha energy (KeV) | Spontaneous Fission (SF) Neutron Emission (n/s) |
|---|---|---|---|---|---|
| $^{229}$Th |  | 7340 | 100 | 5167.6 |  |
| $^{230}$Th | 0 | $7.54 \times 10^4$ | 100 | 4770 |  |
| $^{232}$Th | 0 | $1.41 \times 10^{10}$ | 100 | 4082.8 |  |
| $^{232}$U |  | 68.9 | 100 | 5413.55 |  |
| $^{233}$U | 0 | $1.59 \times 10^5$ | 100 | 4908.6 |  |
| $^{234}$U | 0.187 | $2.46 \times 10^5$ | 100 | 4858.5 | 2.04 |
| $^{235}$U | 7.93 | $7.04 \times 10^8$ | 100 | 4678.8 | $1.19 \times 10^{-1}$ |
| $^{236}$U | 5.53 | $2.34 \times 10^7$ | 100 | 4572 | $3.59 \times 10^1$ |
| $^{238}$U | 925 | $4.47 \times 10^9$ | 100 | 4270 | $1.87 \times 10^4$ |
| $^{236}$Np | 0 | $1.54 \times 10^5$ | 0.16 | 5007 |  |
| $^{237}$Np | 0 | $2.14 \times 10^6$ | 100 | 4959.1 |  |
| $^{238}$Pu | 0.319 | 87.7 | 100 | 5593.2 | $1.08 \times 10^6$ |
| $^{239}$Pu | 5.98 | 24110 | 100 | 5244.5 | $1.28 \times 10^2$ |
| $^{240}$Pu | 265 | 6563 | 100 | 5255.78 | $4.08 \times 10^6$ |
| $^{241}$Pu | 1.75 | 14.35 | 0.00245 | 5140.1 | $3.86 \times 10^{-6}$ |
| $^{242}$Pu | 0.834 | $3.73 \times 10^5$ | 100 | 4984.4 | $1.95 \times 10^6$ |
| $^{244}$Pu | 0 | $8.08 \times 10^7$ | 99.879 | 4665.5 |  |
| $^{241}$Am | 0.0533 | 432.2 | 100 | 5637.8 | $8.75 \times 10^1$ |
| $^{242}$Am | 0.0012 | 141 | 0.459 | 5588.34 | $6.30 \times 10^1$ |
| $^{243}$Am | 0.193 | 7370 | 100 | 5438.1 | $1.52 \times 10^2$ |
| $^{242}$Cm | 0.0162 | 180 days | 100 | 6.12 | $1.14 \times 10^8$ |
| $^{243}$Cm | $8 \times 10^{-4}$ | 29.1 | 99.71 | 6168.5 | $2.48 \times 10^2$ |
| $^{244}$Cm | 0.0882 | 18.1 | 100 | 5901.61 | $1.04 \times 10^9$ |
| $^{245}$Cm | 0.00592 | 8500 | 100 | 5623.5 | $6.61 \times 10^2$ |
| $^{246}$Cm | $7.55 \times 10^{-4}$ | 4730 | 99.9737 | 5474.8 | $6.51 \times 10^6$ |
| $^{247}$Cm | $1.07 \times 10^{-5}$ | $1.56 \times 10^7$ | 100 | 5353.3 |  |
| $^{248}$Cm | 0 | $3.40 \times 10^5$ | 91.61 | 5161.73 |  |
| $^{250}$Cm | 0 | 9000 | 8 | 5169 |  |

By sampling on-line for characteristic neutron (including multiplicity) and alpha emission spectra, the presence or absence (via convolution) of the Pu versus U component can be readily confirmed amidst the mix of isotopes of Cm, Np and Am. Multiplicity refers to a key aspect of fission, that two or more neutrons are released virtually simultaneously, the feature which helps to distinguish neutrons emitted from the actinides which do have multiplicity from those neutrons, including background cosmic neutrons or neutrons released from non-fission processes, that lack multiplicity (i.e. neutron produced one at a time). The level of multiplicity for each actinide of interest is different and can be described by the following equation:

Spontaneous Fission Multiplicity=0.27318Z−22.7734 wherein Z refers to the atomic number of the element. Using this formula, the multiplicity of the actinides of interest can be calculated: Th (Z=90)=1.81, U (Z=92)=2.36, Np (Z=94)=2.9, Am (Z=95)=3.18, Cm (Z=96)=3.45, Cf (Z=98)=3.99. By monitoring the number of neutrons released simultaneously (within no more than a few picoseconds) the respective actinide type can be identified. Unfortunately, known systems, require off-line chemical analyses or counting methods by taking samples to a testing laboratory. Reasonably accurate detection of U and Pu actinides in spent fuel compositions is complicated by the high beta-gamma radiation levels (about $10^{16}$ β or γ/s per assembly at about 1 year after shutdown) and the complexity associated with SNF composition.

In general, fluid metastable states can be reached via tensioning at ambient temperatures. Metastable states can also occur via thermal superheating at high positive pressures followed by depressurization such that fluids become sensitive to incoming radiation and form bubble tracks. When in a metastable state (either tensioned or superheated), explosive phase changes are triggered by stimuli that provide the excess energy required to reach the stability limit at which point the liquid changes phase. Stimuli may include extremely high nucleation rate-inducing nuclear particles such as neutrons, alphas, fission fragments, gamma photons as well as visible (collimated) photons from a laser. The thermodynamic phase spaces associated with tension and thermal superheat-based fluid metastability are depicted in the P-V diagram shown in FIG. 2. As the state of the fluid approaches the stability limits, as shown in FIG. 2 (a.k.a. the spinoidal limits of tension and thermal superheat respectively), the number of nuclei undergoing phase change starts to increase—reaching levels of about $10^{25}$ nuclei/mL·s at the stability limits. As the tension or thermal superheating of the fluid moves away from the stability limits, the addition of excess energy becomes necessary for triggering phase change. Upon triggering of the phase change in metastable fluids, stored energy is released via vaporization growth of fast nucleating vapor bubbles. If the thermal energy deposition rate is sufficient to nucleate a critical size vapor nucleus, generally in the nanometer range, the nucleus will continue to grow into a macroscopic visible vapor bubble.

While bubble chambers and Superheated Drop Detectors (SDDs) operate in the positive pressure superheat regime, Tension Metastable Fluid Detector technology is distinct in its operation in the diametrically opposite regime (i.e., tensioned metastability without superheat). For any given tensioned metastable state far from the spinoidal limit, the required excess energy for triggering phase change of liquids and bubble formation must be provided by energetic ionizing particles such as neutrons, alphas, fission fragments, etc. For a given level of tension metastability, the excess energy required for forming bubbles will furthermore vary with the type and energy of radiation (i.e., neutrons vs alphas vs fission products vs photons), since it is well-known that the linear energy transfer (LET) or dE/dx is strongly dependent on the type of radiation involved, and this can be used to distinguish the types of radiation. This property, which enables macro-mechanical detection of nuclear-scale particles, can be used in ultra-sensitive detectors for nuclear engineering and science applications such as reactor power monitoring, identifying emissions from WMD-based special nuclear materials, or for online monitoring of nuclear spent fuel reprocessing streams where tons of Special Nuclear Materials are processed.

The Tension Metastable Fluid Detector sensor technology is based on placing ordinary fluids such as water or acetone in thermodynamic states of "tension" metastability under vacuum conditions (e.g., −5 bar) at room temperature.

Once the liquid molecule bonds are stretched, excess energy deposited from the direct strike of an energetic particle (e.g., a neutron or alpha particle with energies ranging from keV to MeV) onto a tensioned metastable fluid results in the nucleation of nanoscale bubbles which grow to visible size and then implode back to the liquid state accompanied by audible shock signals and light flashes which can be recorded using conventional electronics. The type and energy of the incident radiation can be assessed by monitoring the energy deposition rate (dE/dx) and the tensioned state and specific properties of the fluid in order to determine the individual actinide species in the mix of nuclear material.

SUMMARY OF INVENTION

Compositions and methods for monitoring the quantity of an actinide present in a test sample are disclosed. The method involves obtaining a test sample for which the knowledge of the actinide amounts is desired and obtaining a tensioned metastable fluid detector having a fluid and a fluid tension level such that the radioactive emission from the actinide can be detected and then determining the amount of the actinide in the sample.

Compositions and methods for monitoring the motion of special nuclear materials through space are also described. The method involves obtaining an acoustically tensioned metastable fluid detector having a fluid and a tension level such that a special nuclear material can be detected and monitoring the direction of the special nuclear material at least at two different times. The difference in the location of the special nuclear material as a function of time then provides an indication of the motion of the special nuclear material through space.

Compositions and methods for monitoring the quantity of a fissile special nuclear material present in a test sample are disclosed. The method involves obtaining a test sample that may contain a fissile special nuclear material. The emission from the sample is then measured using a tensioned metastable fluid detector having a fluid and a fluid tension level such that the fissile special nuclear material can be detected.

Compositions and methods for monitoring actinides during reprocessing of spent nuclear fuel are disclosed. In certain methods the fuel can be monitored after a typical 30-year cool down or waiting period according to Algorithm 1 below. In Algorithm 1 the method for real-time passive monitoring of actinides can include the steps of:
1. procuring a spent nuclear fuel sample of known initial enrichment (i.e. known fraction of $^{235}$U isotope in the uranium fuel mixture);
2. estimating the amount actinides using a computer program, such as Origen;
3. determining actinide masses and spent fuel neutron production ($\alpha$, n) production;
4. calculating a activity of actinides using masses from ORIGEN and Half-life (T½);
5. measuring neutron production with a TMFD system (Calibrated with $^{252}$Cf and PuBe);
6. comparing in real time, the measured neutron production with the predicted neutron production, and if the calculated and predicted neutron production numbers do not agree, re-calibrate the Origen program code input model (e.g., for core-averaged fuel burn up) such that the numbers do agree;
7. extracting a sample from the dissolved fuel and dilute (e.g., to about −0.2 decay per second if near real-time detection is desired to stay within about 5 seconds (=1/0.2)) based on ORIGEN activity estimates of alpha, spontaneous fission and neutron emission;
8. confirming relative absence of $^{242}$Cm activity (i.e. for alpha activity);
9. measuring $^{244}$Cf and determine the concentration of $^{244}$Cm in the sample;
10. measuring combined $^{238}$Pu, $^{241}$Am, and $^{244}$Cm and determine the concentration of $^{238}$Pu, $^{241}$Am in the sample;
11. re-calibrating and refine ORIGEN-S Model for consistency with experimental findings on Cm, Am, and Pu;
12. determining the concentrations of $^{239}$Pu from $^{241}$Am, $^{238}$Pu, $^{244}$Cm as well as ORIGEN code ratios;
13. cross verifying the determined concentrations of $^{239}$Pu from extraction stream by active CTMFD monitoring or CTMFD sipping based monitoring of $^{238}$Pu and $^{239}$Pu.

Compositions and methods for monitoring actinides during reprocessing of spent nuclear fuel after a typical short term cool down period of 180 days are disclosed below in Algorithm 2. In Algorithm 2 the method for real-time passive monitoring can include the following steps:
1. enriching a spent nuclear fuel sample;
2. estimating the amount actinides using a computer program such as ORIGEN-S
3. determine actinide masses and spent fuel neutron production ($\alpha$, n) production, calculate $\alpha$ activity of actinides and T½;
4. measuring neutron production rate and multiplicity (from spontaneous fission) with TMFD system calibrated with $^{252}$Cf and PuBe, compare measured neutron production with predicted neutron production;
5. if the calculated and predicted neutron production numbers do not agree re-calibrate the ORIGEN input model such that the numbers do agree;
6. extracting a sample from the dissolved fuel and dilute (e.g., to about 0.1 to about 10 decays per second, and more preferably about 0.2 decay per second if near real time detection is desired to within about 5 (=1/0.2) seconds) based on ORIGEN activity estimates of alpha, spontaneous fission and neutron emission; then, confirm relative absence of $^{242}$Cm activity (i.e. look for alpha activity), however any detection time can be used for example 1 to 60 or 100 seconds could be used;
7. measuring $^{242}$Cm and determine the concentration of $^{242}$Cm in the sample;
8. measuring combined $^{244}$Cm and $^{242}$Cm and determine the concentration of $^{244}$Cm in the sample;
9. measuring combined $^{238}$Pu, $^{242}$Cm and $^{244}$Cm and determine the concentration of $^{238}$Pu, in the sample;
10. measuring combined $^{238}$Pu, $^{241}$Am, $^{244}$Cm and $^{242}$Cm and determine the concentration of $^{241}$Am in the sample;
11. re-calibrating and refine ORIGEN-S Model for consistency with experimental findings on Cm, Am, and Pu;
12. determine $^{239}$Pu from $^{238}$Pu, $^{241}$Am, $^{244}$Cm and $^{242}$Cm as well as ORIGEN code ratios;
13. cross-verifying the determined concentrations of $^{329}$Pu from $^{241}$Am, $^{238}$Pu, $^{244}$Cm with downstream levels of $^{239}$Pu from Pu extraction stream by active CTMFD monitoring or CTMFD sipping based monitoring of $^{238}$Pu and $^{239}$Pu.

DESCRIPTION OF FIGURES

FIG. 5 provides a graphical representation of Neutron flux ratio versus angular direction for a PU-Be source.

FIG. 6 provides graphical representations of detection time versus $P_{neg}$ (detector fluid tension pressures) for a CTMFD configuration showing the ability to discriminate between neutron energies and emission spectra.

FIG. 10 provides a bar graph showing the variation between neutron yield isotope content from spontaneous fission and α-n reactions: 4 without $^{235}$U; 40 GWd/MTU burn up; 6 month (180 day) Spent Nuclear Fuel cooling period.

DETAILED DESCRIPTION OF INVENTION

Figure 1:
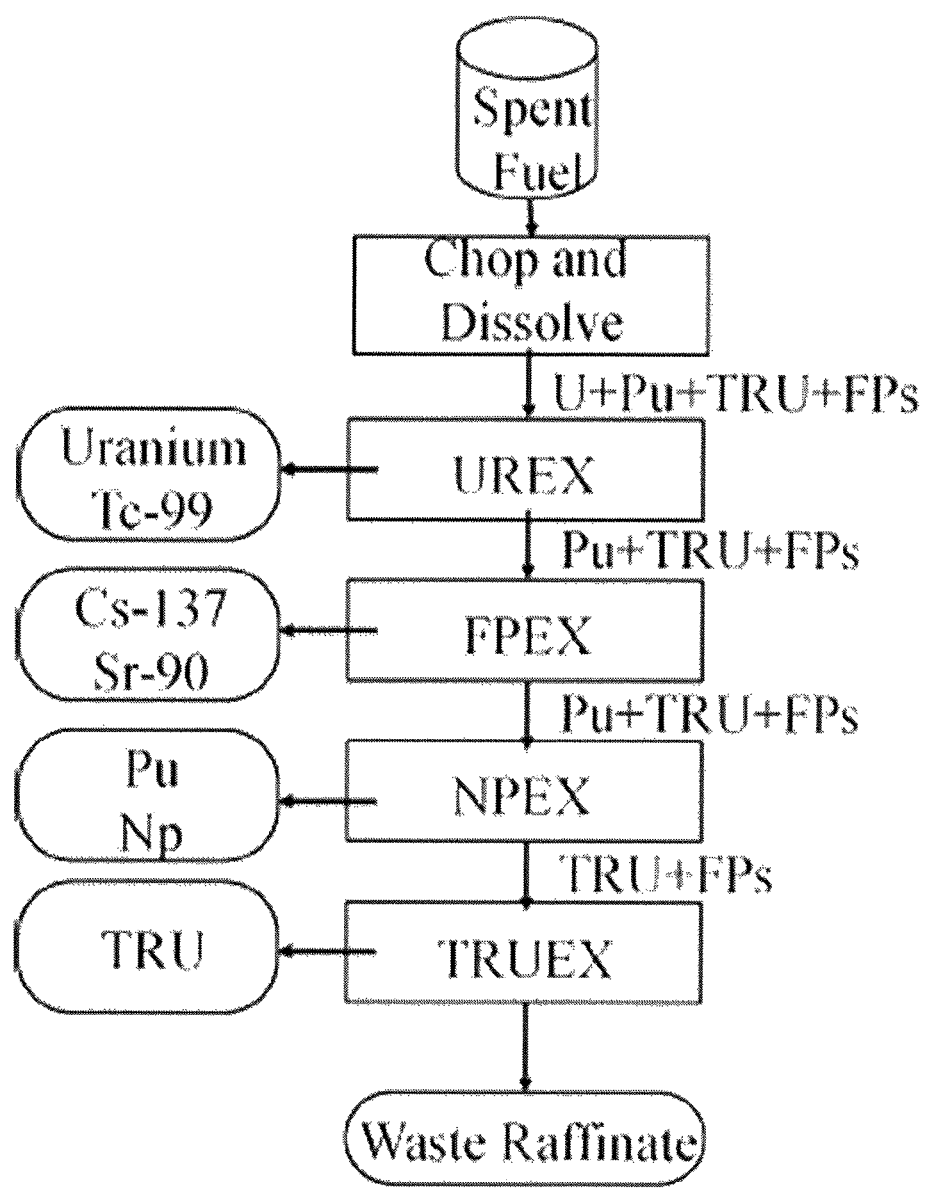
FIG. 1 provides a schematic diagram of a high-level process flow diagram for the UREX+ aqueous separations plan. This is illustrative of the general flow of events during reprocessing; other schemes such as PuREX are similar. The methods disclosed are applicable to any such reprocessing scheme.
Figure 2:
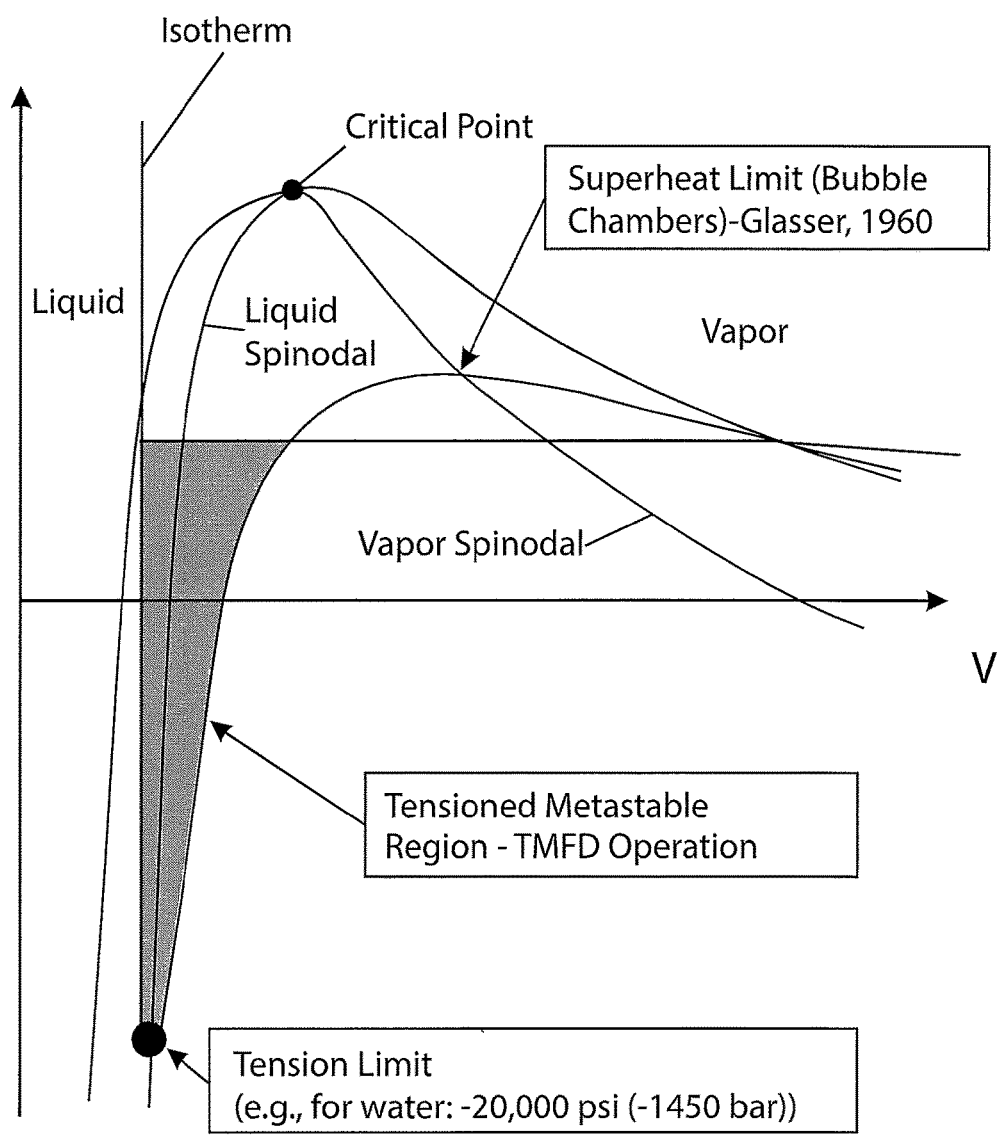
FIG. 2 provides a diagram of showing thermodynamic phase-space for tension and superheated fluid states.

Oak Ridge Isotope Generation (ORIGEN) code, developed by the U.S Department of Energy's Oak Ridge National Laboratory is a nuclear fuel depletion analysis program which was originally developed to monitor for fuel depletion from fission as well as the various fission products over time, and then to monitor for various nuclear reactions and radioactive decay chains which follow. Various versions of ORIGEN have been developed, and when it is used as part of another suite of codes, a suffix is attached, e.g., ORIGEN-S (the "S" depicting the so-called SCALE code package). In this invention, the terms ORIGEN and ORIGEN-S denote the same underlying computer code model.

A composition is disclosed that provides a simple low cost class of sensors with high intrinsic efficiency, for example about 90% or more efficiency, that are able to distinguish between neutrons, alpha particles, and fission fragments and simultaneously also provide directionality and multiplicity related information for neutron emissions from a single, portable sensor system for which the detection efficiency can be controlled. These detectors can physically "see" and "hear" radiation while also deriving spectroscopic information and discerning the direction of incoming radiation and at the same time remain "blind" to gamma photons. The spectroscopic information is acquired using TMFDs by sweeping the tension pressure states ($P_{neg}$) across a range of pressures. At certain pressure points detection of various energy ionizing particles is possible. The ability to remain blind to gamma photons and beta particles allows for use of the device in the intense radiation fields of spent nuclear fuel to decipher neutron and alpha emissions characteristic of U and Transuranic isotopes. Tension Metastable Fluid Detectors remain gamma blind even in the intense field of an operating 1,000 MWe power reactor. Table 2 summarizes certain characteristics of Tension Metastable Fluid Detectors.

TABLE 2

Comparison of Tension Metastable Fluid Detectors vs State-of-Art Systems

| Parameter | State-of-Art Systems | TMFD System |
| --- | --- | --- |
| Size, standoff Size: physical dimensions of detector; Standoff: how far the detector is from the source of radiation | Limited to small sizes (cost exponentially increases with size) | Can be tailored to situation (single large system) |
| Intrinsic efficiency: (The fraction of incident radiation passing through the detector that is actually detected) | ~10-20% (MeV neutrons); ~90% (thermal neutrons for 30 cm × 30 cm) | ~90% (MeV neutrons and thermal neutrons). |
| On-Off times (How long it takes for the detector system to switch on and off) | Large (minutes) | Microseconds |
| Gamma blind? | No; systems can get saturated in high gamma fields | Yes; No saturation problems. |

TABLE 2-continued

Comparison of Tension Metastable Fluid Detectors vs State-of-Art Systems

| Parameter | State-of-Art Systems | TMFD System |
| --- | --- | --- |
| Directionality/Direct Source Imaging: (The ability to characterize the shape and size - like taking a picture) | No. | Yes (to within 10° for directionality; also, for Special Nuclear Materials source imaging |
| Cost | High (>$10K for simplest systems). | Low-to-modest ($0.1K to $1K). |
| Complexity | Large; requires complex electronics. | Low; Can actually see and hear radiation in the form of collapsing bubbles. |
| Same system for neutrons, photons, alphas? | No. Require specialized systems for each particle type. | Yes. Same system can be tailored to detect neutrons, photons and alphas. |
| Multiplicity with single detector system? | No. Requires multiple systems and complex electronics. | Yes (also aids in identifying Special Nuclear Materials as opposed to cosmic and other background radiation). |

Multiplicity as it pertains to neutron emission comprises two or more simultaneous (i.e., occurring so fast within pico to femto seconds that for practical purposes are deemed to be simultaneous) neutron emissions which occur only during fission events as compared with randomly generated neutrons from either radioactive decay or from non-fission nuclear reactions (like alphas striking nuclei of elements like Be, B, Li, F, O). Fission of U, Pu and other fissile elements produces different numbers of neutrons in each fission event. Hence, this method provides only detection of fissile materials but also identification of the specific element type. Neutron multiplicity capability for a detector is the ability to detect two or more neutrons arriving into the detector simultaneously. In ordinary detectors which are enclosed and based on counting scintillation light pulses or charge pulses and without the enablement of monitoring of the individual strikes, such events get detected as being from a single event. In the TMFD system, the occurrence of two or more simultaneous bubble formations within the TMFD volume becomes conspicuous and can be recorded using a single imaging and/or electronic recording system. In this regard, we have, as noted earlier, provided for the multiplicity values for various actinides of interest ranging from Th to Cf. A single TMFD can detect and reveal arrival of simultaneous neutron emission. This makes the TMFD far more efficient for deciphering the specific element compared with conventional detectors.

The multiplicity (for spontaneous fission) varies from less than 2 to close to 4 for Cm and Cf. The multiplicity ($v(E_n)$) value can be increased by increasing the energy of external neutrons ($E_n$) used for interrogating a given mass of fissile materials. In this case, ($v(E_n)=v(0)+aE_n$ where, a varies with the nuclide in question [i.e., a=0.1419 ($^{235}$U); =0.1482 (U-238); =0.1432($^{237}$Np); =0.1471 ($^{239}$Pu); =0.1482 ($^{241}$Am); =0.1536 ($^{244}$Cm)]. For example, one usually has available portable D-T accelerators which produce 14 MeV neutrons. If we use 14 MeV neutrons to decipher the presence of $^{235}$U, for example, the value for $v(14)$ for $^{235}$U induced fast neutron fission would equate to about 4.5 (versus about 2.36 for spontaneous fission); similarly, with 14 MeV neutrons, the induced fission with $^{239}$Pu would move up from about 2.9 (spontaneous fission) to about 5. Multiplicity-based determination can be accomplished more efficiently using multiple TMFDs surrounding the interrogated item to increase the solid angle subtended onto the source of materials.

Figure 3:
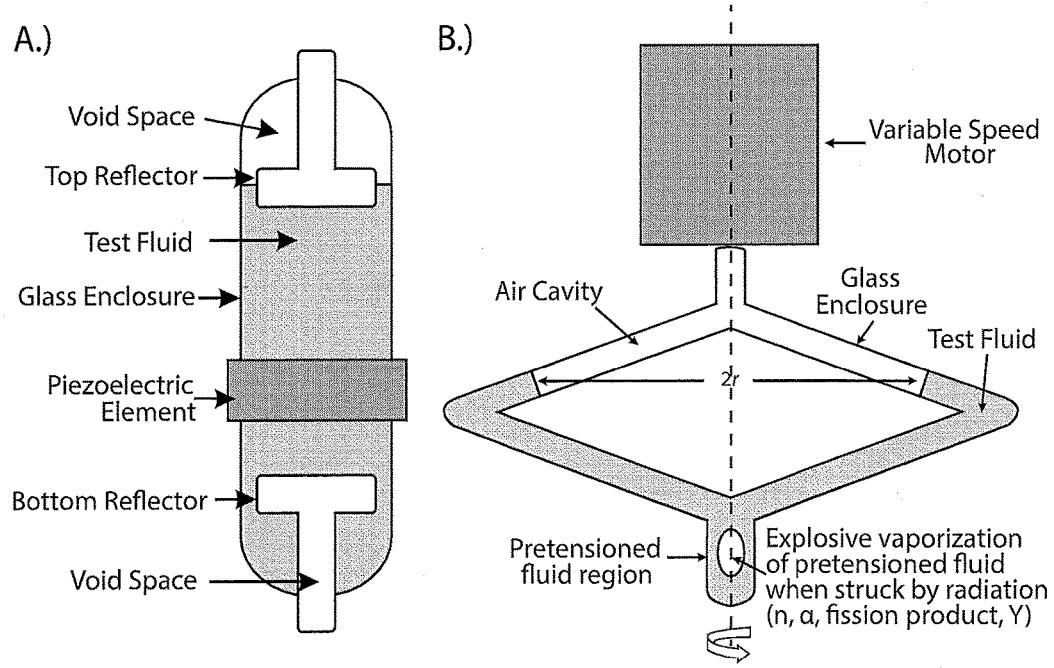
FIG. 3 provides schematic diagrams of Tension Metastable Fluid Detector systems where the metastable tension in the fluid is induced via: (a) induced oscillating pressure fields and (b) centrifugal motion.

FIG. 3 shows schematic diagrams for two types of Tension Metastable Fluid Detector systems that have been developed and qualified in laboratory experiments. The Acoustically Tensioned Metastable Fluid Detector (AT-MFD) shown in FIG. 3a uses piezoelectric elements to induce time-varying acoustically-driven oscillating pressure fields (compression and tension) in a resonance mode at micro-second time scales much like a laser cavity. When in the tension mode, the fluid field nucleates bubbles in transient fashion when nuclear particles provide sufficient energy. As such, the ATMFD turns on and off within microseconds. Interestingly, while in compression mode the system remains completely blind to all forms of radiation which is important in pulsed (neutron/photofission) based monitoring. Conventional detectors saturate during the pulsing time span and continue to remain blind for considerable periods of time after pulsing; therefore, losing important emission signatures. The ATMFD's unique features allow it to overcome such dead-times. The location and timing of the bubbles provides information on type, multiplicity, energy and directionality of the nuclear radiation.

In another embodiment, tension metastable states in fluids are created with centrifugal force. These detectors are useful in centrifugal tension metastable fluid detector system. FIG. 3b of the centrifugal tension metastable fluid detector system depicts an enclosure constructed from glass tubing formed into a diamond shaped apparatus. The apparatus is partially filled with a working liquid of density ρ and meniscus separation 2r and attached to a variable speed motor. Upon rotation, centrifugal force pulls the molecules outward effectively placing the molecules in the central bulb region in a tensile state. The level of tension or negative pressure $\rho_{neg}$ on the centerline is given by the following equation.

$$\rho_{neg} = 2 \times \pi^2 \times \rho \times r^2 \times f^2 - \rho_{amb}$$

where, f is the rotational frequency and $\rho_{amb}$ is the ambient pressure. As a first order approximation, the pressure variation in the central bulb region can be modeled as flow between two cylinders rotating with the same velocity where the inner cylinder has a radius of zero. This approximation reduces the equation to the Bernoulli equation. For the small bulb radii used in CTMFD apparatus the pressure variation in the central bulb region is negligible. Both system designs are amenable to scalability to enhance overall efficiency and sensitivity.

The Tension Metastable Fluid Detector systems can be used to monitor trace, such as sub-picoCurie/mL, actinide quantities via direct sampling in real-time and with spectroscopic information at levels about 100 times below the resolution of liquid scintillation spectrometry. This is clearly shown in FIG. 4, as example of the detection within about 35 s of U isotopes in the 0.015 Bq/g (equal to about 0.4 pCi/mL) range. The CTMFD volume was about 2 cc. This activity level was found to be below electronic background noise and indistinguishable when tested in a LS6500 Beckman spectrometer. Also, by merely increasing the size of the central CTMFD bulb by a factor of 10, e.g., from about 2 cc to about 20 cc, one could readily get similar turnaround results in about 35 s for 10-fold lower activity, e.g., even at 0.04 pCi/mL levels. The data points shown in FIG. 4 represent averaged values. Radioactivity, being a random process, necessarily implies a Poisson distribution; e.g., at about 35 s wait time, the spread can be expected to be about +/−6 s representing about 70% of all measured counts for 1 standard deviation. In this regard, a Tension Metastable Fluid Detector system can be used to distinguish between $^{241}$Am and $^{238}$Pu alpha recoil emissions, which are only about 2 keV apart, and the same system can also detect spontaneous fission events.

Figure 4A:
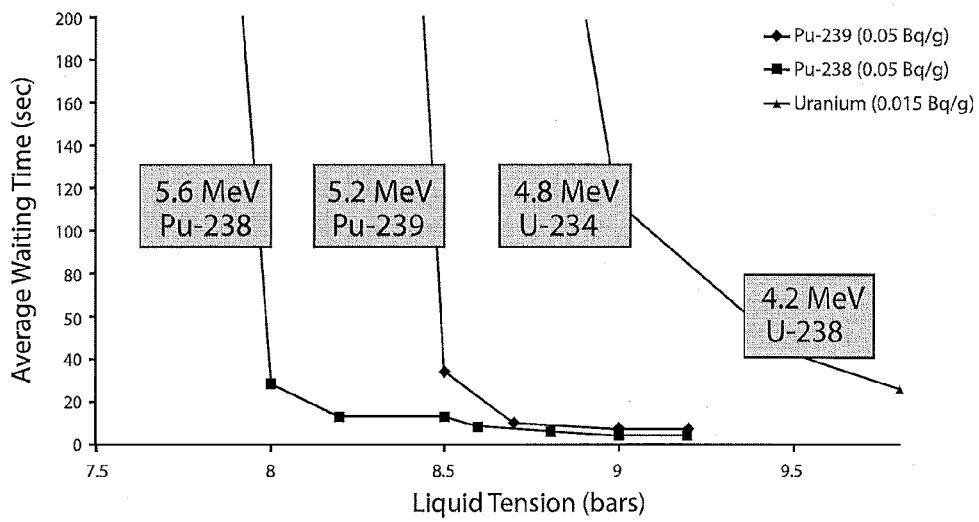
FIG. 4 shows the results of alpha spectroscopy with Tension Metastable Fluid Detectors with NIST-certified actinides (Note: Loess is a smoothing algorithm)
Figure 4B:
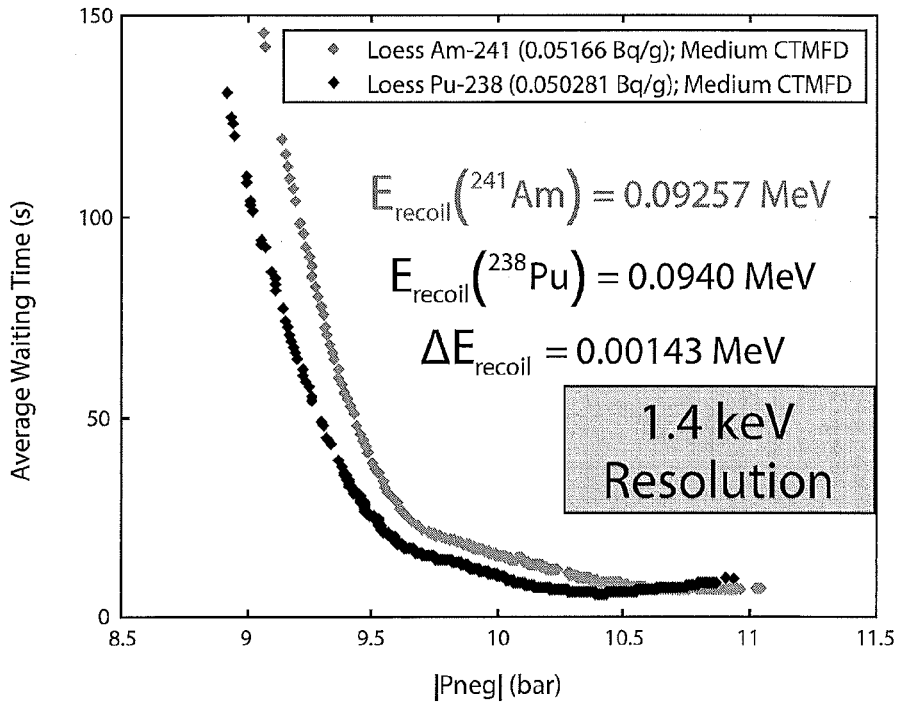

FIG. 4a illustrates the detection of trace actinide bearing samples having only about 0.05 Bq/cc. Special Nuclear Materials that include actinides ranging from $^{238}$Pu, $^{239}$Pu, $^{241}$Am, $^{234}$U, and $^{238}$U can be detected and monitored by tailoring the specific level of tension metastability. These data were obtained using NIST-calibrated sources. Separately, FIG. 4b illustrates that the about 2 keV separation between actinide recoil energies can be observed for trace-level isotopes virtually in real time.

A method is also disclosed for monitoring neutron emissions with greater than 90% intrinsic efficiency, and with ATMFDs for discerning the direction of a Pu—Be neutron source (±about 30°) with 90% (FIG. 5). This evidence formed the basis for extending the technology not only for real-time neutron source directionality, but also for simultaneous source imaging such that the actual motion through space of Special Nuclear Materials can be monitored and tracked.

Monitoring can also distinguish between fission-induced neutron multiplicity and random neutron events. This surprising possibility was observed where 8-fold greater multiple neutron-induced events were recorded when using a relatively weak spontaneous fission source (i.e., $^{252}$Cf) of about $10^5$ n/s strength, in contract to when a Pu—Be random neutron emitting (about $10^6$ n/s) source was used. This provides a basis for discerning between fissile Special Nuclear Materials (U to Pu to Cm) from their multiplicity signature differences and rejecting extraneous random events (e.g., the well-known "Ship-Effect"). As noted earlier, fission events lead to neutron multiplicity, whereas, neutron emissions from radioactive decay and non-fission nuclear reactions lead to randomly produced non-simultaneous neutron emissions.

The Tension Metastable Fluid Detector is blind to gamma radiation while detecting neutrons and alpha radiation for fields greater than about $10^{11}$ γ/s, which is equivalent to the gamma field about 5 m away from a spent fuel assembly after about 6 months of cooling. It has been estimated that Tension Metastable Fluid Detectors that are tailored for alpha, neutron, or fission fragment detection can remain blind to energetic gamma photons even within the core of an operating 3,000 MW(t) nuclear reactor.

The gamma flux in a 3,000 MW(t) nuclear fission reactor is well-known to be in the range of about $10^{14}$ γ/cm$^2$/s. The generation of detectable bubble events in TMFDs requires a certain threshold level of energy in the range of about 100 keV deposited by a recoiling carbon or oxygen type nuclei within the dimensions of the critical radius of about 70 nm. The maximum energy produced from a typical 1 MeV nuclear reactor gamma photon on to nuclei such as H and C can at most be 0.5 keV per collision. Studies based on pulsed nanosecond lasers and theoretical assessments indicate that gamma photon influence on to TMFDs if placed within an operating power reactor could only take place if the power level and hence, the photon flux, were to be over $10^{23}$ γ/cm$^2$/s—which is a billion times greater than in existing nuclear reactors.

A Tension Metastable Fluid Detector systems for Near Real Time Accountability monitoring of key Special Nuclear Materials for Pu, in particular for $^{239}$Pu; other uranium species, especially $^{235}$U; and Cm actinides in various sections of a reprocessing plant are disclosed.

The principal isotopes of interest for security purposes are $^{239}$Pu and $^{235}$U, both fissile isotopes. While both of these isotopes are abundant in mass in Spent Nuclear Fuel, neither their alpha nor spontaneous fission activity levels are high enough (relative to the background radiation levels in Spent Nuclear Fuel) to be readily detectable. The high background alpha and neutron emissions in Spent Nuclear Fuels arise principally from the formation of $^{242}$Cm, $^{244}$Cm, $^{241}$Am and $^{238}$Pu. The level of background from these isotopes are, in general, at least an order of magnitude greater than the alpha or neutron activity of $^{239}$Pu, and several orders of magnitude greater than that of $^{235}$U. This could readily be overcome by resorting to active interrogation using an external neutron source because the fission cross-section of $^{239}$Pu is large, for example greater than about 600 barns, and the mass quantity of $^{239}$Pu is orders of magnitude greater than that for the Cm and Am isotopes. However, such a procedure, although enabling and possible to undertake, requires use of an external neutron or photon source such as a D-D or D-T accelerator for neutrons, or an electron linear accelerator (LINAC) for photons, or, use of isotope neutron sources such as $^{252}$Cf or Pu—Be or Am—Be "together" with TMFD banks. This can raise the overall system costs and complexity (e.g., accelerator systems can cost upwards of $100K to $1 M) and hence, would not be as economic or portable (due to their weight and fragile electronic components) as using simple passive means which relies mainly on TMFDs and PC-based processing algorithms alone. Therefore, in the absence of active monitoring, e.g., neutron or photon-based fission of the target substance, indirect quantification of the amounts must be used. This is especially relevant for $^{239}$Pu, the Pu isotope of greatest interest found in a nuclear explosive device Importantly, the International Atomic Energy Agency (IAEA) has set the threshold limit for the "significant quantity" of Pu (including all isotopes) at just 8 kg. The quantity of $^{239}$Pu in Spent Nuclear Fuel is difficult to determine in the initial reprocessing steps because $^{239}$Pu is mixed with extremely high levels of fission products. The high levels of beta-gamma activity in SNF, including radiation intensity fields of over 100 R/h, make it virtually impossible for present-day sensors (e.g., $^3$He detectors) to provide meaningful information on actinide content in general, much less $^{239}$Pu levels.

A Tension Metastable Fluid Detector system can be used to monitor the collection of actinides (including $^{239}$Pu) at the highly-sensitive front-end of the PuREX/UREX reprocessing streams since it is gamma-beta blind, while remaining selectively sensitive with over about 90% efficiency for detecting alpha recoils, neutrons and fission fragments from actinides.

The described methods rely in part on the following assumptions:

The original $^{235}$U enrichment in the Spent Nuclear Fuel (i.e., prior to fission) is known. This value is readily and contractually available to the nuclear power utility from the fuel vendor and hence, is a known quantity with little to nil uncertainty.

The power history of the fuel assembly is known as it was operated in the reactor over a given period of time while producing power. These data are often preprogrammed by the utility during the development of core management schemes, and records are kept for control rod motion and sensors during any particular cycle. This parameter influences the degree of fuel burn up throughout the core. Although the power history in a 3-D sense is reasonably known, unforeseen circumstances such as reactor scrams or other aspects requiring temporary reactor shutdown can give rise to variations. Hence, a margin of uncertainty results—the degree of which must be quantified via actual measurements for key actinides (e.g., $^{242}$Cm, $^{244}$Cm, $^{241}$Am, $^{238}$Pu, $^{235}$U, $^{239}$Pu) in order to then correct for the averaged burn up for a given SNF assembly or assemblies which are dissolved in a vat ahead of reprocessing.

The cool down period of the Spent Nuclear Fuel is known and available from the data logs kept by the nuclear power utility. This parameter is known with good confidence and hence, with minimal uncertainty.

The ORIGEN-S depletion code is available to simulate (with reasonable accuracy) the burn up history and buildup of actinides and fission products. ORIGEN-S is a computer code widely utilized worldwide and available from the U.S. Department of Energy (USDoE's) Oak Ridge National Laboratory, Oak Ridge, Tenn., USA. ORIGEN-S has been validated extensively and also separately against data for this application as discussed subsequently.

As part of the real-time on-line monitoring with Tension Metastable Fluid Detector Systems, the validity of the ORIGEN-S code as a virtual simulator to provide a first-cut estimate of Special Nuclear Materials actinide content in Spent Nuclear Fuels was tested. It was useful to assess how well predictions compare with reasonably well characterized post-irradiation-examination data. Argonne National Laboratory and Pacific National Laboratory and Oak Ridge National Laboratory staff have conducted assessments for such situations and, post-irradiation-examination on several light-water-reactor Spent Nuclear Fuels in 2007, referring to these samples as Approved Testing Materials (ATM) as part of a DoE program for developing experimental material for nuclear waste repository researchers. Utilizing the information on power history, initial enrichment and cool down histories, ORIGEN-S based models were developed for predicting fuel depletion and the generation of key actinide inventories over time. A sample of comparison against ATM-103 Spent Nuclear Fuel specimen is shown in Table 3. As noted in Table 3, the ratio of ORIGEN-S to post-irradiation-examination values is within +/−8% for the mix of actinides; importantly, for $^{239}$Pu and $^{235}$U the comparison is within 3% to 1%, respectively.

TABLE 3

Comparison of Predicted (ORIGEN-S) and PIE Data - PWR Fuel burn up for a 30 MWd/MTU (average); 2.72 wt. % enrichment; 6.5 y cooling time.

| Nuclide | ORIGEN (kg/MTU) | PIE (kg/MTU) | ORIGEN/PIE |
|---|---|---|---|
| $^{241}$Am | 0.377 | 0.382 | 0.99 |
| $^{237}$Np | 0.404 | 0.373 | 1.08 |
| $^{238}$Pu | 0.157 | 0.168 | 0.93 |
| $^{239}$Pu | 4.9 | 4.75 | 1.03 |
| $^{240}$Pu | 2.42 | 2.4 | 1.01 |
| $^{241}$Pu | 0.901 | 0.922 | 0.98 |
| $^{242}$Pu | 0.594 | 0.621 | 0.96 |
| $^{234}$U | 0.143 | 0.136 | 1.05 |
| $^{235}$U | 5.38 | 5.42 | 0.99 |
| $^{236}$U | 3.63 | N/A | N/A |
| $^{238}$U | 947 | 955 | 0.99 |

The above comparisons show that, if the detailed power history, initial enrichment and cool down history are known with good confidence (e.g., core averaged burn up of fuel to within +/5%) for each Spent Nuclear Fuel, a reasonable estimate of $^{239}$Pu and $^{235}$U actinides (with over 95% confidence) can be made. However, detailed accurate information may not always be available, and even a seemingly small deviation of 3% of mass inventory from a total annual inventory of 1,000 kg could amount to about 30 kg or more for $^{239}$Pu which significantly exceeds the IAEA safeguards limit of 8 kg. Therefore, based on the results of ORIGEN-S validation studies, estimated predictions of inventory of various actinides should only be used as a simulation tool as part of a mix, to arrive at a first estimate. The mix refers to a combination of prediction and in-situ real time data acquisition via TMFD data for confirmation and refinement of the predictive tool as described above in Algorithms 1 and 2 to arrive at a first estimate. But, for on-line monitoring in real-time, the threat of potential diversion requires a real-time verification-correction tool that offers a means to continually cross-check and update to refine the primary assumptions used to make ORIGENS-based predictions. Tension Metastable Fluid Detector technology can be used for this purpose, in tandem with ORIGEN-based predictions.

From a practical viewpoint, there are two types of Spent Nuclear Fuels for reprocessing each requiring a somewhat distinct algorithm of steps for discerning the key $^{235}$U and $^{239}$Pu isotopes as described in the Algorithms. These include: (1) legacy fuel with 2-3 wt. % enrichment with 20-30 GWd/MTU burn up followed by a 30-year cool down, and (2) more modern fuels with a 4-5 wt. % enrichment with burn ups up to 50 GWd/MTU followed by a 0.5-year cool down period. The significance of these differences in light of relative actinide buildup is in terms of buildup of $^{241}$Am, $^{242}$Cm and $^{238}$Pu (both strong alpha emitters but weak spontaneous fission neutron emitters), and $^{244}$Cm (a strong alpha and spontaneous fission neutron emitter).

For the first Spent Nuclear Fuel type with 30-year cool down, the relative activity of $^{241}$Am, $^{244}$Cm and a $^{238}$Pu far outpaces the strength of $^{242}$Cm, whereas for the second Spent Nuclear Fuel type with only a 0.5-year cool down period, the relative buildup of $^{241}$Am is negligible and the dominant alpha-neutron activity is from $^{242}$Cm, $^{244}$Cm and $^{238}$Pu.

The significant differences in the actinide buildup of the two types of Spent Nuclear Fuel, as mentioned above, demand unique monitoring strategies depending on the fuel type. The two types of Spent Nuclear Fuel, however, will also possess certain commonalities, which are listed in this section ahead of two specifically targeted algorithm-based methods targeted to Near Real Time Accountability at the front-end. The two algorithms are described above. Common features between the two monitoring schemes are presented (along with estimated time of task completion).

First, information obtained from the nuclear utility is introduced into ORIGEN and is used to develop an estimate of the relative quantities of different actinides, including estimates for a range of potential burn up levels. This should only require a few minutes to accomplish using for example, a personal computer based system.

Second, Tension Metastable Fluid Detector systems are used to monitor the Spent Nuclear Fuel at the initial stages of reprocessing to determine the quantity of $^{239}$Pu. The amount of $^{239}$Pu can be determined based on monitoring of neutron activity in the presence of a very strong beta-gamma dominated radiation background that can be as high as about $10^9$ Ci (for a typical PWR using about 40 T of U and about 3-5 wt. % enrichment) in total at cycle end before cool down on a core average basis (comprising about $10^{20}$ γ-β/s, about $10^{17}$ alpha/s, and about $10^{10}$ n/s). The SNF can be dissolved in nitric acid and placed in a vat prior to further reprocessing. The alpha particles cannot penetrate to the outside of the bath, but the neutrons, gammas and to a small extent the beta rays will penetrate. If a conventional detector is placed outside such a vat, the gamma to neutron flux would be about $10^{10}$:1 (i.e., over 10 billion times higher gammas compared with neutrons). Known detectors such as $^{213}$Ne and $^3$He based detectors are limited in that they can reliably detect neutrons without gamma interference at most if the gamma to neutron fluxes are in the range of about 10:1 to about $10^3$:1. When these detectors are used in initial measurements of SNF a major uncertainty remains in terms of the quantity of actinides present, particularly $^{239}$Pu and $^{235}$U. Such uncertainty complicates monitoring the material as it passes through various processing stages. SNF from a typical PWR core at end of cycle can generate close to 500 kg of $^{239}$Pu, and substantially smaller quantities are considered a threat for the development of nuclear explosives. Moreover, at end of cycle not all of the $^{235}$U is consumed. About 500 kg of $^{235}$U remains which far exceeds what is considered a threatening level for nuclear explosives.

If knowledge about the quantities of actinide species can be made available right up front and throughout reprocessing procedures SNF could be handled more confidently and safely. A neutron detector that can detect neutrons with about 90% efficiency or more and that remains blind to gamma-beta radiation for use in monitoring SNF is disclosed. TMFDs offer such a capability. TMFDs using detection fluids such as acetone, isopentane, methanol, ethanol, trimethyl borate, perfluoroctane, R-113 and operated with $P_{neg}$ down to about -20 bar have been demonstrated to remain totally gamma blind. They have also been observed to have over 90% of the theoretically attainable intrinsic efficiency for neutron, alpha and fission product detection. As a result the systems and methods described herein can be used to determine the quantity of $^{239}$Pu and other actinides present in SNF.

For SNF that is delivered to the reprocessing plant, the isotopic inventory which dominates the spontaneous fission neutron rate is $^{244}$Cm with an emission intensity of about $5\times10^8$ n/s/MTU (0.5-year cool down fuel) and about $10^8$ n/s/MTU for 30-y cooldown fuel. For the Spent Nuclear Fuel the resultant neutron output will be about 3% to 10% greater due to the additional $^{244/242}$Cm(α,n)$^{16}$O reactions from the fuel being in UO$_2$ oxide form, but the ORIGEN assessment includes this factor resulting in approximately an additional $3\times10^7$ n/s (0.5y cool down fuel) and about a $3\times10^6$ n/s (30y cool down fuel). This addition of an (α,n) source to the spontaneous fission neutron source gives rise to a neutron spectrum that is a combination of two weighted spectra and can be readily accommodated. In this step, a pre-calibrated centrifugal tension metastable fluid detector (with a commercially available $^{252}$Cf, spontaneous fission source of certified intensity, together with a commercially available PuBe or AmBe type source of about 3 to about 10% of the $^{252}$Cf neutron intensity can be utilized at various distances from the pipe or vat holding the Spent Nuclear Fuel. Such a step provides the first sensor-based data for the presence of $^{244/242}$Cm to update the ORIGEN simulation. This estimate may be further refined by extracting a small quantity of dissolved SNF and placing it in a TMFD system with a fluid such as acetone as the detection fluid and assessing for fission activity from spontaneous fission. The amount of extraction will depend upon the degree of dilution of the SNF. For 30y cool down fuel with about a 3 wt. % enrichment and 30 GWd/MTU burn up for example, the neutron production rate per MTU is estimated as: $^{241}$Am about $1\times10^3$ n/s; $^{242}$Cm about $3\times10^4$; $^{244}$Cm about $8\times10^7$ n/s; $^{238}$Pu about $2.6\times10^5$ n/s; $^{239}$Pu about 80 n/s; and $^{240}$Pu about $2\times10^6$ n/s. Clearly, $^{244}$Cm dominates in fission activity with all else being negligible by comparison. This means that the detection of $^{244}$Cm fission activity can be used to determine the relative quantities of other actinides as well. This can be readily determined by diluting the extracted fluid from the vat such that the expected fission activity is about 100 fissions/second based on the previously detected neutron activity as a whole. As shown in FIG. 6, the fact that the alpha activity for this sample will be several orders of magnitude higher does not interfere with this determination when the $P_{neg}$ value of the TMFD is set such that the TMFD is sensitive only to fission events and blind to neutrons as well as alpha events. This can be seen in FIG. 6. By placing about 0.1% by volume of this actinide bearing fluid into 100 cc of acetone the resulting solution will have a "fission" activity of about 0.1 Bq/cc. This solution can be placed in a 1 cc TMFD at a $P_{neg}$ of about -1 bar, and the TMFD will detect each fission event while remaining blind to alpha, neutron, gamma as well as beta activity. This measurement can be used to determine actual actinide activity levels together with the neutron measurements. For 180 day cool down fuel (40 GWd/MTU, 4 wt. % enrichment) the neutron activity from spontaneous fission is dominated by $^{244}$Cm (about $5\times10^8$ n/s/MTU) and also $^{242}$Cm (about $1.3\times10^8$ n/s/MTU) with the output from other actinides about similar to that for 30y cool down fuel except for $^{241}$Am which is negligible. In this instance, the dilution steps would be similar to that taken for 30y cool down fuel followed with placing the TMFD system to a $P_{neg}$ of about -1 bar to count for fission activity from Cm. Unlike for 30y cool down fuel, this measurement provides for the combined activity of $^{242}$Cm and $^{244}$Cm even though $^{244}$Cm activity for fission is about 5-fold higher for fission activity (not alpha activity). For 0.5y cool down fuel, the alpha activity is in fact dominated by $^{242}$Cm (about $1\times10^{15}$ alphas/s/MTU) whereby, the $^{242}$Cm:$^{244}$Cm alpha activities are in the ratio of about 5:1. This too could be readily ascertained. However, the same solution prepared for fission rate estimates would need to be diluted by a further factor of about 10 million times. For such a diluted system, alpha activity would now dominate and the $P_{neg}$ can be swept from about -6 bar through -8 bar to then decipher for the activities first, for $^{242}$Cm and then, for $^{244}$Cm, respectively. This step may take approximately one to ten minutes to accomplish in a practical situation once the calibrated TMFDs are in place and tied in with the ORIGEN simulation platform.

Information from the detector system is used to make fission and neutron measurements which are then compared with the ORIGEN-predicted buildup of $^{244/242}$Cm (the major source of neutron emission); in case of discrepancy, the Spent Nuclear Fuel averaged burn up would be adjusted such that the updated ORIGEN prediction for $^{244/242}$Cm is commensurate with the measured value. Since the fundamental nuclear physics governing the burn up process builds up the other actinides in specific consort with $^{244}$Cm, this raises the confidence level of a best-estimate up front for all other actinides of interest, $^{241}$Am, $^{244/242}$Cm, $^{238}$Pu and, especially for $^{239}$Pu. Information from this step also provides the level of dilution of the actinide-rich fluid stream that will be necessary to dissolve within the working fluid of the Centrifugal Tension Metastable Fluid Detector for monitoring alpha activity from the various actinides. This can be done using a computing device.

Figure 7:
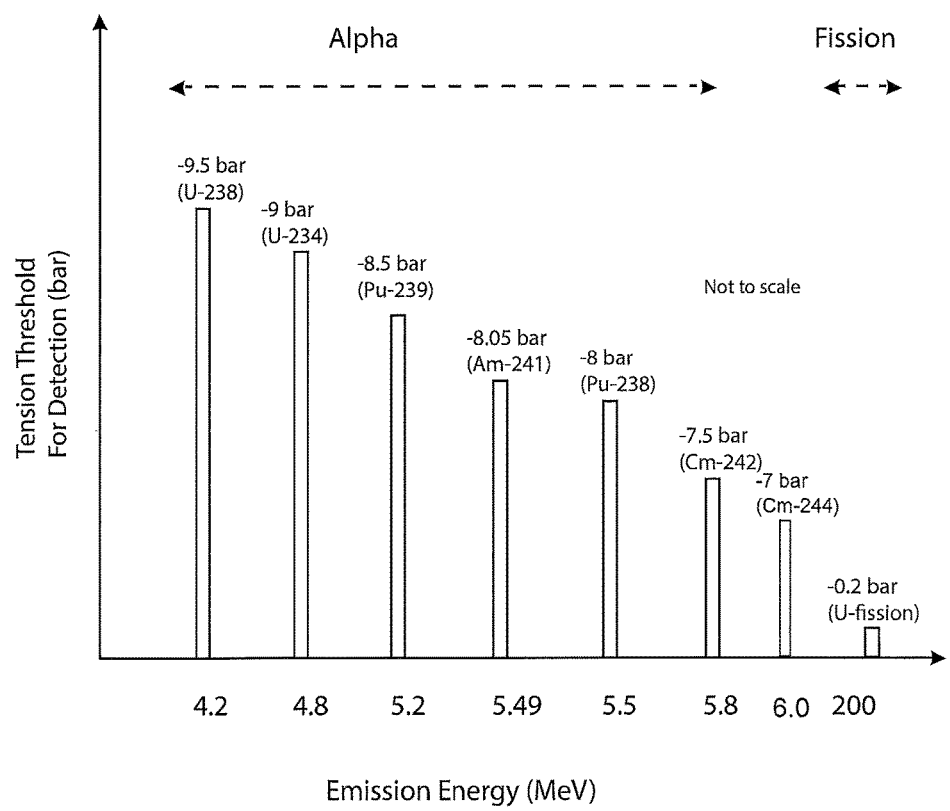
FIG. 7 graphically depicts tension thresholds for Pu, U, Cm and Am isotopes using a single Tension Metastable Fluid Detector system.
Figure 8:
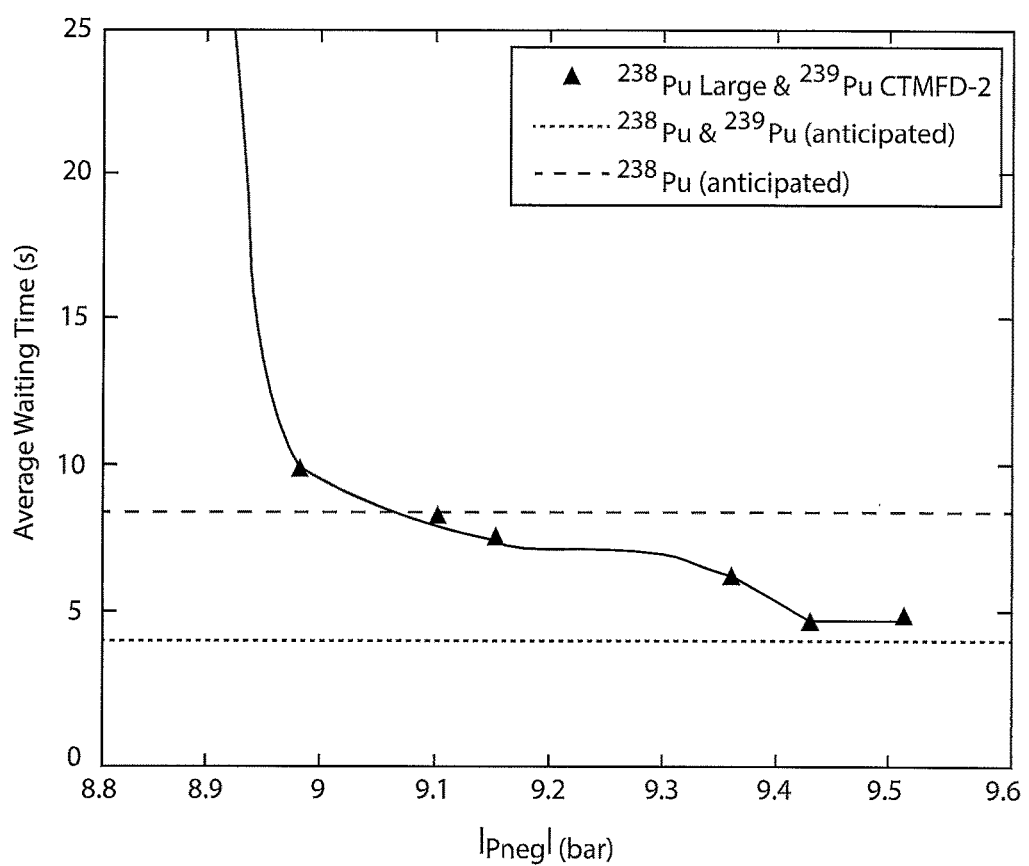
FIG. 8 provides a graphical depiction showing the relationship between the average signal waiting time in a Tension Metastable Fluid Detector and a fluid tension for various actinides.
Figure 9:
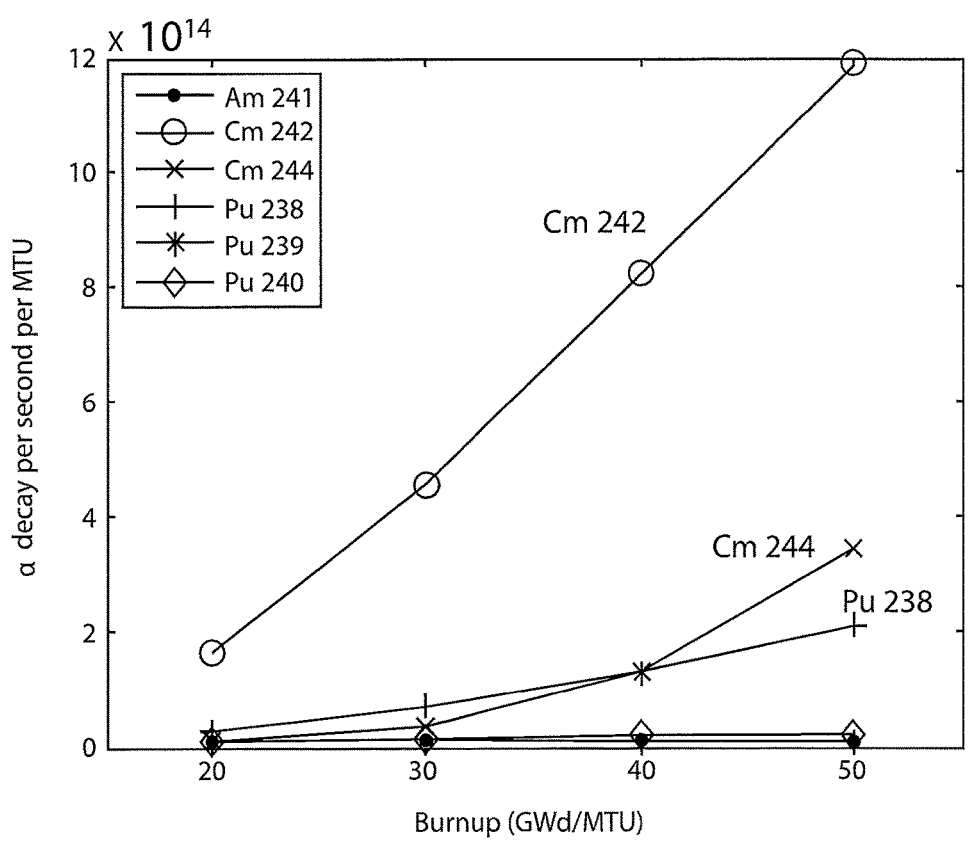
FIG. 9 depicts the relationship between a decay/sec/MTU and burn up (GWd/MTU) for various actinides over a 180 day cooling period.
Figure 11:
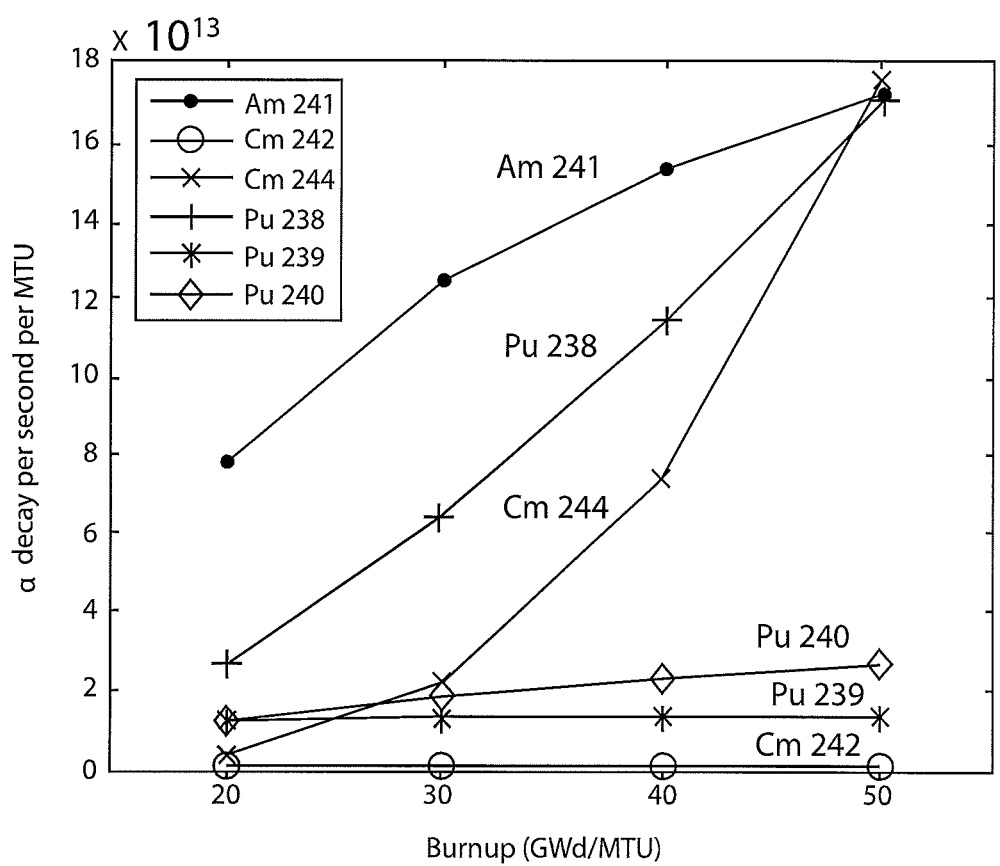
FIG. 11 graphically depicts the relationship between α yield and burn up over a 30 year cooling period for various elements in spent nuclear fuel.
Figure 12:
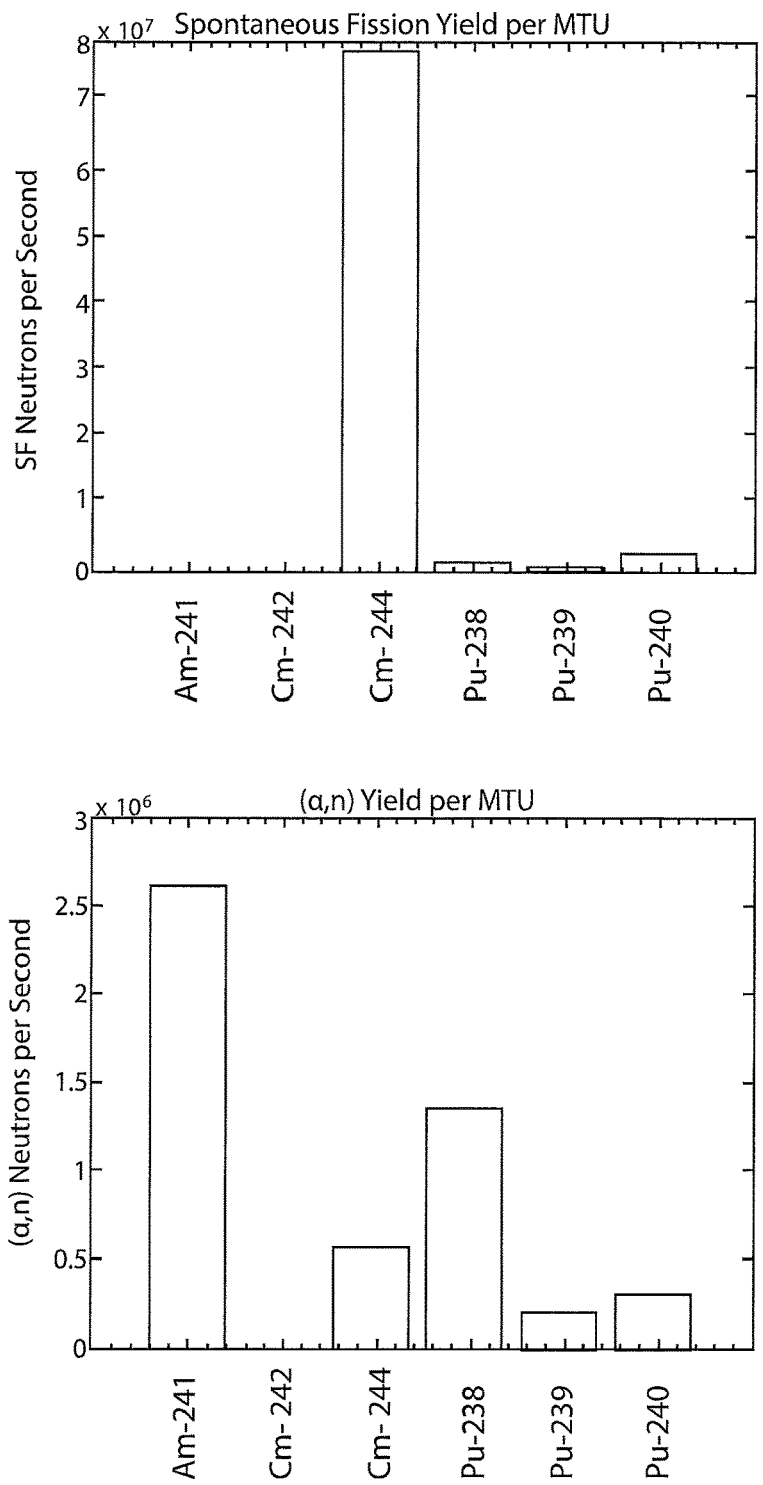
FIG. 12 graphically depicts the relationship between neutron yield with isotopic content from spontaneous fission and α-n reactions: 3 without $^{235}$U; 30 GWd/MTU burn up over a 30 year Spent Nuclear Fuel cooling period.

The next measurement will involve directly measuring alpha activity. This involves removing a small quantity of SNF bearing reprocessing fluid. The amount of sample to remove is an amount that provides for suitable data acquisition times. The extent of dilution by the plant operator must also be known. Alpha activity in a given volume of reprocessing fluid is estimated on a per MTU basis. One MTU (in oxide form as is the case for virtually all nuclear power reactors) assumes a volume of about 10 L. Assuming a 10:1 dilution the resultant initial alpha activity would be: about $2 \times 10^{10}$ Bq/cc (0.5y cool down fuel) and, about $2 \times 10^9$ Bq/cc (30y cool down fuel). If detection of activity is to be about 10 s on average, the activity within a TMFD, such as a CTMFD having a sensitive volume about 1 cc can be set to be about 0.1 Bq (total activity). This means, the reprocessing fluid stream activity must be diluted (e.g., by over $2 \times 10^{11}$ times for 0.5y cool down fuel and by about $2 \times 10^{10}$ times for 30y cool down fuel) to bring down the resultant activity in the TMFD fluid to about 0.1 Bq/cc (of TMFD fluid). For example, an aliquot (e.g., 1 µL) can be removed from the vat holding the dissolved Spent Nuclear Fuel, and diluted with acetone (as was done previously with NIST-certified standards) or with other suitable TMFD fluids such as ethanol, and methanol. The degree of dilution can be directly estimated based on the expected total activity such that the overall activity after dilution is in the 0.1 Bq/cc range for this example. Since the dilution is performed using the TMFD detection fluid (e.g., isopentane, acetone, methanol, or ethanol for example) the quantity of SNF reprocessing stream fluid in the TMFD fluid volume is negligible and far less than 1%. Levels of about 1% of nitric acid will not affect the TMFD detection. Assuming the centrifugal tension metastable fluid detector volume being used is 2 cc and the activity of the highest energy alpha emitting isotope $^{242}$Cm is 0.01 Bq/cc in the diluted solution, the time it will take to determine the presence of $^{244}$Cm would be about 50 seconds at a tension level of about −6.5 bar to −7.5 bar (per FIG. 7). If the activity of $^{244}$Cm is also 0.01 Bq/cc., then, the tension metastability level should be adjusted to sweep between −7 bar to −8.5 bar to detect the combined activity of $^{242}$Cm and $^{244}$Cm within 25 seconds. As shown in FIGS. 6-7 the negative pressure range can be scanned with a single centrifugal tension metastable fluid detector sensor to determine the amount of various actinides in a step-wise progressive fashion (i.e., first for $^{242}$Cm which emits alphas at 6.1 MeV; then for $^{244}$Cm which emits alphas at 5.8 MeV; then for $^{238}$Pu at 5.5 MeV; then for $^{241}$Am at 5.49 MeV, and so on).

TMFDs can be calibrated for specific detection of the actinide species described above or other radiation sources. The specific values for $P_{neg}$ associated with detecting the actinides (alpha emitting isotopes) shown in FIGS. 4-8 can be determined for any CTMFD or ATMFD system via calibration using NIST-certified sources. Small variations between TMFDs may occur and should be accounted for. Variations in a CTMFD can occur due to the central bulb not being axi-symmetric, as well as due to meniscus separation in the upper arms, the uncertainty in density due to temperature of operation, and other reasons. The meniscus separation, for example, involves taking an average of the outer and inner edges of the meniscus from each of the two arms. If the radius of separation is assumed to be from the outer edges, the resulting $P_{neg}$ as computed (for a given density and rotational speed) will be greater than if the separation distance is assumed to between the inner edges of the meniscus. A consistent approach should be adopted to build up a calibration plot for time needed for detection of samples of NIST-certified (known) activity for specific actinide isotopes. These calibrations can easily be carried out by those of skill in the art.

Typically, the $^{238}$Pu:$^{239}$Pu activity ratio is about 10:1. While $^{238}$Pu can be determined within about 10 s, to detect for $^{239}$Pu requires about 10-fold longer times of about 100 s; while still attainable directly, cosmic neutron induced background effects of about 0.0065 n/cm$^2$/s should also be accounted for. The $^{235}$U activity in the overall process stream is normally expected to be much lower due to its half-life being about 1,000 times greater, although the total $^{235}$U mass at end of the cycle may be similar to that for $^{239}$Pu. This makes direct assessment for $^{235}$U in the overall process stream (upfront) somewhat impractical. While monitoring for $^{239}$Pu may be feasible, as mentioned above, the monitoring for $^{235}$U could only be carried out in the subsequent UREX stream (wherein, the U elements are preferentially diverted) and upon which higher alpha energy emitting elements of Cm, Am and Pu are absent. Overall, due to the significantly lower relative alpha activity of the $^{239}$Pu and $^{235}$U actinides, in order to monitor $^{239}$Pu and U-based isotopes directly, a centrifugal tension metastable fluid detector with a significantly larger sensitive volume of about 100 cc as shown in FIG. 3B must be used. In such an embodiment, the dimension of the radial separation term "2r" in FIG. 3B must be increased such that, variations of tension metastability within the central bulb are relatively small (e.g., about 1-5%) when compared with the overall variations between the central region and that at the end of the arms. In accordance with well-established laws of physics governing fuel burn up and isotope decay, and highly precise information relating to the dependence of $^{239}$Pu and U-isotope quantities on the quantities of $^{244}$Cm, $^{242}$Cm, $^{241}$Am and $^{238}$Pu in the mixture, the levels of $^{239}$Pu and U-isotopes can also be determined. In order to expedite this, multiple CTMFDs working in parallel may be readily arranged in the system and used at $P_{neg}$ values that distinguish between different elements or subsets of elements and their quantitation.

The aforementioned steps can be accomplished within one to three hours. In comparison, current techniques used for materials accountability require several weeks and must be accomplished off-site at specialized laboratories. Therefore, the presently described TMFD systems will provide an extreme improvement in the speed, accuracy, timeliness and cost of actinide detection.

There are nuances when separately applying the above steps for 30-year and 0.5-year cool down fuel types.

In the 30-year fuel having about 30 GWd/MTU burn up and 3 wt. % enrichment the impact of $^{242}$Cm (162-day half-life) is negligible because its alpha activity would be about 100-fold lower. However, due to decay of $^{241}$Pu ($^{241}$Pu→$^{241}$Am+β−) a significant accumulation of $^{241}$Am should be accounted for. Even the $^{244}$Cm (17.6-year half-life) activity would not be as dominant, and yet, it would be possible to detect its activity within the mix of nuclides since, the computed representative activity ratios of $^{241}$Am:$^{244}$Cm is about 6:1. This means that if $^{241}$Am is detectable within 1 second for example, $^{244}$Cm would be detectable within about 6 seconds on average.

In this instance the relative alpha activity ratios of several key actinides from depletion physics are known (calculated via ORIGEN-S for 3 wt. % enrichment and 30 GWd/MTU) to be: $^{241}$Am to $^{238}$Pu=about 2:1; $^{241}$Am to $^{244}$Cm=about 6:1; $^{241}$Am to $^{239}$Pu=about 10:1; and, $^{238}$Pu to $^{239}$Pu=about 5:1.

Using the disclosed centrifugal tension metastable fluid detectors, $^{241}$Am and $^{238}$Pu and $^{244}$Cm can be readily monitored, although this may take more time to detect (i.e., compared with that for $^{241}$Am). For example, even if the relative activity of $^{241}$Am alone in the sampled mixture is only about 0.1 Bq in the centrifugal tension metastable fluid detector and the associated activities for the other actinides would be: $^{244}$Cm (0.017 Bq=0.1/6); $^{238}$Pu (0.05 Bq=0.10/2); and $^{239}$Pu (0.01 Bq); the mixture activity would be the sum equal to about 0.177 Bq. Therefore, scanning from lower tension to higher values, the time to detect and ascertain the various nuclides would be: about 60 s (=1/0.017) for $^{244}$Cm alone; followed with about 15 s [=1/(0.017+0.05)] for $^{238}$Pu and $^{244}$Cm; about 6 s [=1/(0.017+0.05+0.1)] for $^{241}$Am together with $^{244}$Cm and $^{238}$Pu, and, theoretically, about 5.65 s [=1(0.017+0.05+0.1+0.01] for $^{239}$Pu together with the other three. This process makes it readily possible to estimate for $^{239}$Pu content both directly (i.e., by actual measurement by scanning the $P_{neg}$ space for threshold $P_{neg}$ requirements for detection of specific energy alpha recoils from various actinides as shown in FIG. 7, first starting with $^{244}$Cm activity (at lowest Pneg of about −7 bar), then for $^{244}$Cm+$^{238}$Pu (at a higher $P_{neg}$ of about −8 bar), then for $^{244}$Cm+$^{238}$Pu+$^{231}$Am activity (at a subsequently higher $P_{neg}$ of about −8.1 bar) and then for $^{244}$Cm+$^{238}$Pu+$^{231}$Am+$^{239}$Pu (at a further subsequent higher $P_{neg}$ of about −8.5 bar), and via confirmatory association with the underlying nuclear physics fuel depletion and isotopic decay i.e., via established laws of nuclear physics as encoded within ORIGEN which dictate that, for a given burn up SNF and cool down history, if one knows of the activity of any one of the key constituents, e.g., $^{244}$Cm, then, the other constituent isotopes of interest must also be present in certain proportions—unless some type of diversion has taken place. The method for making such assessments is provided in the bullet list below.

Method for monitoring during reprocessing of actinides from spent nuclear fuel after 30-year cool down as described in Algorithm 1.
  Enrichment; Net Average; Burn up; Cooling Period—The process starts by collecting information from the nuclear power plant that is the origin of the SNF, so the initial fuel enrichment of $^{235}$U is known. Also the core-average burn up of the SNF is known because this is pre-determined ahead of starting the nuclear reactor based on a prescribed optimized pattern, and the amount of time the SNF was held in a cooling pool or dry cask ahead of transmittal to a reprocessing plant is known. From these three metrics, only the core-averaged burn up would entail a certain level of uncertainty due to the fact that the rate of fuel fission in an actual operating reactor varies over about 1 to 2 years of power generation. However, during reprocessing the very first step involves combining a distributed burn up pattern into a combination averaged mass via nitric acid dissolution. This leads to a measure of uncertainty which must then be addressed via actual measurement down the processing stages; however, up front, a good first estimate of the various activities can be made using the well-established ORIGEN code system.
  Estimate the amount of actinides using ORIGEN-S/run model—per the aforementioned information, within seconds, the ORIGEN-S code system can provide a table of actinides and their relative activity levels.
  Determine actinide masses, spontaneous fission (SF)/ Neutron Production, (Alpha, n) Production—Based on the ORIGEN model predictions, neutron production from spontaneous fission and also from alpha interactions with mixture elements (principally with O atoms) can be determined. The total neutron production represents an estimate of the actinide inventory and vice-versa.
  Calculate Alpha Activity of actinides using masses from ORIGEN and T½-Similar to the earlier step for neutron production, by knowing the elemental composition as predicted by the ORIGEN code model, and knowing the half-lives for alpha decay for the actinide elements, the activity of each actinide can be calculated using the formula: Activity in curies per gram (Ci/g)= $(0.693/T_{1/2}) \times 1.6 \times 10^{13}/A$, where A=atomic mass of the actinide of interest and $T_{1/2}$ is the half-life.
  Measure neutron (including for fission rate) production with CTMFD (Calibrated with $^{252}$Cf and PuBe) for comparison with prediction—In this step, a TMFD (e.g., a CTMFD) calibrated for neutron detection efficiency is used to determine the fission spectrum and random spectrum neutrons. $^{252}$Cf represents a good fission spectrum source of neutrons, whereas, PuBe or AmBe isotope based sources produce random (in time) spectra neutron sources from (alpha, n) nuclear reactions. Both, $^{252}$Cf and PuBe or AmBe sources are available in the marketplace with certifications of their strengths. These sources can be used to calibrate the CTMFD for efficiency of detection of neutrons in fission and also mixed type (fission and random) source environments. The calibrated CTMFD can then be positioned a set distance away from the front-end vat containing the dissolved contents of SNF and the intensity of neutron emission can be measured. This measurement can readily be completed within minutes using a CTMFD with a sensitive volume in the multi-cc (about 200-500 cc) range, although an ATMFD could also be used. The intensity of neutron emission forms a measure of how much activity has built up during burn up of a given level Importantly, as mentioned earlier, during this front-end stage, the background activity from beta-gamma decay are about 10 orders of magnitude greater than that for neutron activity, and can saturate most commonly available neutron detectors in the marketplace (e.g., $^3$He, $BF_3$, etc.). Hence, known detectors fail to provide information on actinide activity level from their neutron signals. TMFD technology, on the other hand, remains completely blind to gamma-beta radiation when using TMFD fluids such as acetone, isopentane, perfluorooctane, ethanol, methanol, trimethyl borate and R-113 and the $P_{neg}$ states are kept above about −20 bar. The measurement provides at least about 90% intrinsic efficiency at detecting neutrons with detectors that are sized to permit about 2 mean free path dimensions for neutrons entering the TMFD sensitive volume (e.g., about 10 cm diameter, and 5-10 cm height). For assessment of fission activity, the CTMFD system may be small, in the range of about 1 cc sensitive volume. The dilution of the SNF solution and detection for fission activity for deriving the actual $^{244}$Cm content by utilizing $P_{neg}$ in the −1 bar range (wherein it remains blind to neutrons, alphas, gammas and betas) while remaining more than 95% efficient for detecting fission fragments has been discussed earlier. The neutron production rate is 3.45-fold higher than the $^{244}$Cm fission rate and this number can be used to confirm the detection rate for neutrons as a whole. For 30y cool down fuel, $^{242}$Cm should have decayed down considerably such that its alpha activity (which, at 180 day cool down was 5-fold higher than for $^{244}$Cm) is 100-fold lower than that for $^{244}$Cm. This can be readily verified by further dilution of the fission signature mixture by an additional 100,000-fold such that $^{244}$Cm can be detected within seconds but detection of $^{242}$Cm takes 100-fold longer when the $P_{neg}$ is increased to about −8 bar. The relative contents of the other isotopes of interest can be determined thereafter.

Re-Calibrate ORIGEN until the measured neutron production agrees with the ORIGEN estimate—As discussed above, an uncertain upfront metric for ORIGEN code model calculations involved the averaged SNF burn up during its residence time within the nuclear power reactor. Using this averaged estimate, a measure of actinide activity and hence, neutron output can be predicted. The higher the burn up, the higher the actinide activity buildup and consequently, the higher the neutron generation rate. The aforementioned step of actually measuring for the actual neutron emission intensity offers a strong basis for correcting for the average SNF burn up such that the predicted and measured neutron intensity levels agree. Once this is done, the total actinide inventory comprising the key (Cm, Am, Pu and U) isotopes is established. The precise amounts can be confirmed during subsequent stages and can be tracked for possible diversion.

Extract samples from dissolved fuel and dilute to about −0.2 decay per second per cc with acetone or other suitable solvents, diluting according to ORIGEN estimation of activity—Per the neutron measured activity based correction, the ORIGEN predicted alpha activity would be known to a good first order of activity. Only small (microgram) quantities of in-process fluid mixtures are required at this stage for extraction and subsequent dilution in the TMFD host fluid material (e.g., acetone) such that the desired (per ORIGEN predicted) activity level is in the 5 Bq/cc range. The precise level is unimportant and this value is used for illustrative purposes since, at 5 Bq/cc, detection for alpha activity in total could be done within 0.2 seconds. With a more moderate 0.1 Bq/cc activity level, the detection would take about 10 seconds on average.

Confirm the absence of $^{242}$Cm—A key confirming indicator for a 30y cool down fuel is the relative absence of $^{242}$Cm. This is a due diligence step and can be carried out by placing the fluid mixture in the CTMFD and noting for any alpha activity at/around $P_{neg}$ of about −6.5 bar; there the wait time for detection should conclusively be greater than a prescribed pre-calibrated amount that includes cosmic background effects in a 1-2 cc CTMFD system (e.g., about 60 seconds).

Measure the amount of $^{244}$Cm and verify for the presence of $^{242}$Cm at 100-fold reduced activity—Once $^{242}$Cm for the sample is confirmed as being negligible (i.e., detectable), one now increases the $P_{neg}$ to about −7 bar through −8 bar to note the relative activity of $^{244}$Cm. As an enhanced control, from a separate sample from the same reprocessing stream but diluted less (e.g., if the prior dilution was to 0.2 Bq/cc, this confirmation sample may be diluted to provide about 20 Bq/cc) and measured for $^{242}$Cm activity by establishing the $P_{neg}$ of the CTMFD to about −6.5 bar to −7 bar. The laws of nuclear physics governing fuel burn up and activity buildup require that the activity of $^{242}$Cm should now be detectable. This provides an additional and simultaneous control.

Determine the concentration of $^{244}$Cm—using the data for activity for $^{244}$Cm measured from the previous step which involved the illustrative 5 Bq/cc sample.

Measure combined amounts of $^{238}$Pu, $^{241}$Am, and $^{244}$Cm—Since the $P_{neg}$ values for $^{238}$Pu and $^{241}$Am are close enough (i.e., about −8 bar) the $P_{neg}$ value of the CTMFD can be increased to −8 bar to −8.5 bar to effectively determine the combined activity of $^{244}$Cm, $^{238}$Pu and $^{241}$Am.

Determine the concentration of $^{238}$Pu and $^{241}$Am—Subtract the activity of the combined measurements from that for $^{244}$Cm alone to then derive an estimate for the combined amount of $^{238}$Pu and $^{241}$Am.

Re-Calibrate and refine ORIGEN-S Model for consistency with experimental findings on Cm, Am, and Pu—the relative activity levels of these three isotopes can be compared with the activity levels predicted by ORIGEN to obtain a more certain estimate of these levels.

Determine [$^{239}$Pu] from [$^{241}$Am], [$^{238}$Pu], [$^{244}$Cm] as well as ORIGEN Code ratios.

Cross verify this determination with downstream levels of $^{239}$Pu (in Pu extraction stream) via active measurement and or CTMFD sampling with monitoring of $^{238}$Pu and $^{239}$Pu

| Actinides | Ratio [in activity/MTU; 30 y cool down; 30 GWd/MTU; with 3 wt. % enrichment |
|---|---|
| $^{241}$Am/$^{238}$Pu | 2:1 |
| $^{241}$Am/$^{244}$Cm | 6:1 |
| $^{241}$Am/$^{239}$Pu | 10:1 |
| $^{238}$Pu/$^{239}$Pu | 5:1 |

Method for monitoring of actinides during reprocessing for spent nuclear fuel after a 180-day cool down. The following steps are essentially the same as that discussed above for 30-y cool down fuel. The principal exceptions being that, for the 180 day cool down fuel, the alpha rate is dominated by $^{242}$Cm, the fission neutron rate is dominated by $^{244}$Cm (with this rate being about 5-fold greater than that from $^{242}$Cm), and the alpha and fission neutron emission rates from $^{241}$Am are negligibly small.

Enrichment; net average burn up; cooling period.
ORIGEN-S/Run Model on PC.
Actinide Masses SF Neutron Production (Alpha, n) Production.
Calculate alpha activity of actinides using masses from ORIGEN and T½.

Measure neutron production with CTMFD (Calibrated with $^{252}$Cf and PuBe) for comparison with prediction.

Re-Calibrate ORIGEN until it agrees with measured values.

Extract samples from dissolved fuel and dilute to about ~0.2 decays per second (for fission activity monitoring and separately, also for alpha activity monitoring) with acetone according to ORIGEN estimation of alpha-activity. Acetone is a convenient universal solvent liquid to choose; however, other suitable liquids include (e.g., ethanol, methanol, R-113, isopentane, etc.) and can be used so long as the SNF mixture is soluble.

Measure for $^{242}$Cm activity from alpha activity monitoring; for $^{244}$Cm from fission activity.

Determine concentration of $^{242}$Cm from measured activity.

Measure combined $^{242}$Cm and $^{244}$Cm.

Determine concentration of $^{244}$Cm.

Measure combined $^{238}$Pu, $^{242}$Cm, and $^{244}$Cm.

Determine concentration of $^{238}$Pu.

Measure combined Am-241, $^{238}$Pu, $^{242}$Cm, and $^{244}$Cm.

Determine concentration of $^{241}$Am.

Re-Calibrate and refine ORIGEN-S model for consistency with experimental findings on Cm, Am, and Pu.

Determine concentrations of $^{239}$Pu from $^{241}$Am, $^{238}$Pu, $^{242}$Cm, and $^{244}$Cm as well as ORIGEN Code ratios.

Cross verify with downstream levels of $^{239}$Pu in the Pu extraction stream via active monitoring and/or CTMFD sipping based monitoring of $^{238}$Pu and $^{239}$Pu.

| Actinides | Ratio of alpha activities (with 5 wt. % enrichment, 50 GWd/MTU burn up, 0.5 y cool down) |
|---|---|
| $^{244}$Cm/$^{238}$Pu | 1:1 |
| $^{242}$Cm/$^{244}$Cm | 5:1 |
| $^{242}$Cm/($^{244}$Cm + $^{238}$Pu) | 2:1 |
| $^{238}$Pu/$^{239}$Pu | 10:1 |

Compared to 30-year cool down Spent Nuclear Fuel, the $^{241}$Am content in 0.5 year cool down Spent Nuclear Fuel is negligible, but the impact of $^{242}$Cm should be included because its 0.5y half-life would not have allowed significant decay. The relative alpha activity ratios from depletion are as follows: $^{244}$Cm to $^{238}$Pu=about 1:1; $^{242}$Cm to $^{244}$Cm=about 5:1; $^{242}$Cm/($^{244}$Cm+$^{238}$Pu)=about 2.5:1; and, $^{238}$Pu to $^{239}$Pu=about 10:1. The neutron activity levels (n/s/MTU) from spontaneous fission are dominated by $^{244}$Cm as noted: $^{241}$Am (9.8×10); $^{242}$Cm (about 1.3×10$^8$); $^{244}$Cm (about 5×10$^8$); $^{238}$Pu (about 5.5×10$^5$); $^{239}$Pu (89) and $^{240}$Pu (2.5×10$^6$).

Furthermore, as noted above, the total neutron emission rate of about 5×10$^8$ n/s/MTU is largely from Cm with the intensity ratio based on Spontaneous Fission half-lives $^{244}$Cm to $^{242}$Cm about 5:1. Interestingly, $^{242}$Cm activity while not as high as $^{244}$Cm is readily discernible from the activity levels of $^{244}$Cm and also $^{238}$Pu. Since the activity of $^{241}$Am is negligible, there is less chance for interference when monitoring for $^{238}$Pu with its closely spaced alpha energy emission; therefore, the quantity of $^{239}$Pu is more confidently obtained for 0.5-year cool down Spent Nuclear Fuel compared with 30-year cool down Spent Nuclear Fuel. The methods for such assessments are provided in the following paragraphs.

The sensor system and structure comprising Tension Metastable Fluid Detector sensor hardware are combined with ORIGEN-S based simulation and prediction methods for monitoring Pu, U, and other actinide isotopes, at initial processing stages (as described above) and through subsequent stages in a chemical nuclear reprocessing plant. For tasks that involve mixing the SNF bearing solution with the TMFD fluids, such as for direct monitoring of fission and alpha rates, dilution will be necessary. The degree of dilution must be estimated. For this, the following series of steps can be used:

The gamma-beta activity (A) in SNF can be estimated from the formula, A (Bq)=P×10$^6$×[t$^{-0.2}$−(t+T)$^{-0.2}$]×3.7×10$^{10}$, where, P is the thermal power in megawatts, T (in days) is the duration of operation of the reactor at that power level, and "t" is the time (in days) after shutdown of the reactor. For example, for a typical 3,000 MW reactor, shutdown after operating for 18 months, at "t=180" days after shutdown will have gamma-beta radioactivity A of about 10$^{19}$ Bq. This is the gamma-beta activity in the SNF which is typically about 40 tons, although this can vary by about 2-fold. Therefore, the beta-gamma activity per MTU would be about 2×10$^{17}$ Bq/MTU. Since this activity is mainly gamma-beta variety, and gamma photons can be readily measured by conventional detectors such as NaI, the level of activity per MTU on average can be estimated even at the front end—note: this does not provide any reasonable information relating to the actinide content. Since the density of UO$_2$ is about 10$^5$ kg/m$^3$, the volume per MTU of SNF prior to dissolution would be about 40×10$^3$/1×10$^5$ or, about 0.4 m$^3$. Assuming the SNF is diluted by 100-fold, the specific activity (gamma-beta) per MTU would amount to about 6×10$^{11}$ Bq/MTU/cc Once the total activity level per unit volume in the dissolved SNF vat is known the dissolved SNF must be diluted for gamma-beta blind neutron, fission and alpha activity monitoring. For 180 cool down fuel: the alpha activity per MTU is estimated to be about 10$^{15}$ Bq/MTU; the neutron activity level dominated by Cm isotopes is about 5×10$^8$ neutrons/sec/MTU (from which the fission activity is readily obtained by dividing by the multiplicity factor for Cm which is about 4, to result in fission activity rates of about 10$^8$ fissions/sec/MTU). The alpha activity is about 200 times lower than the gamma-beta activity, whereas, the fission activity is about 2×10$^9$ times lower than the gamma-beta activity in the SNF vat.

For efficient detection in the TMFDs the dilution can be performed with acetone. The TMFD detection capability with a given detection fluid (e.g., acetone) can be significantly reduced if significant quantities of inorganic fluids such as water or nitric acid are used. The addition of about 1 to 5 vol. % of inorganic liquids does not impair performance if the TMFD fluid is acetone. This additional volume of inorganic substances may be increased even to about 10 vol. % by mixing isopentane with acetone. However, for SNF vat mixtures of the type discussed above the inclusion of SNF bearing inorganic fluids such as HNO$_3$ should not pose an issue. For TMFD systems meant to monitor for fission rates and alpha rates, the TMFD's sensitive volume may be kept low (e.g., 1 cc) since the track lengths of alphas and fission fragments can be expected to be no more than a few tens of microns at most. Also, for detection within a reasonable amount of time (e.g., within 10 seconds on average), the fission or alpha activity per cc should then be about 0.1 Bq/cc. This implies that, for 180-day cool down fuel, under the above-mentioned conditions, and assuming that we add 1 vol. % to the TMFD volume, the SNF in the vat must be diluted by a factor of: for alpha activity monitoring dilute by about 200/0.01 or $2\times10^4$; for fission activity monitoring dilute by about $2\times10^9/0.01$ or about $2\times10^{11}$.

An optimal reprocessing system for generating new fissile fuel for energy generation should efficiently and securely separate key elements such as U, Cm, Pu into various radioactive waste streams. For example, from FIG. 1 one (UREX) stage involves removal of U and $^{99}$Tc from the balance of fission products and transuranics. It is important to ensure that such separation occurs as intended and that quantities of actinides such as Cm and Pu are not inadvertently diverted into this stream. Therefore, in U/Tc bearing streams, monitoring for $^{235}$U, $^{238}$U and $^{99}$Tc helps to ensure the "absence" of Cm, Pu, Am-type actinides.

An assay for the various isotopic separations is described. The method utilizes instrumentation for conducting assays in real time. In one method a Tension Metastable Fluid Detector monitoring system can include at least two detector banks. The first bank can include a calibrated Tension Metastable Fluid Detector for monitoring neutrons from spent fuel spontaneous fission and α-n reactions, where the predicted intensity is calculated to be in the range of about $2.5\times10^8$ n/s/MTU, and about $5\times10^8$ n/s/MTU for 30-year (~30 GWd/MTU burn up and 3 wt. % enrichment) and 0.5-year (about 40 GWd/MTU burn up and 5 wt. % enrichment) cool down Spent Nuclear Fuels, respectively. Both fuel sources are dominated by $^{244}$Cm. The relative contribution to neutron production from α-n reactions varies from about 3% for 30y cool down fuel to about 10% for 0.5y cool down fuel. Monitoring can provide a basis for estimating the quantity of $^{244}$Cm and the amount of the rest of actinides of interest can be calculated from this using the disclosed methods. The neutron detector bank would preferably include 2 CTMFDs with sensitive volumes in the 300-500 cc range and using detection fluids such as isopentane and trimethyl borate so that the instrumentation can monitor with at least 90% intrinsic efficiency. Although one such CTMFD would suffice, having two CTMFDs should enable backup detection and/or to cross-check the reading of the other.

In an embodiment the second bank can contain at least 4 Tension Metastable Fluid Detectors each operating at tension metastable states connected with detection of key isotopes $^{244}$Cm, $^{242}$Cm, $^{238}$Pu, and $^{241}$Am. Considering that this second bank pertains to detection of fission fragments and also for alpha emitters via sampling and dilution, the central sensitive volume of the CTMFD may be as small as 1 cc. This is because the fission fragments and alpha particles and recoil atoms get readily stopped within the detection fluid within several tens of microns. A sampling system can be used to draw a quantity of fluid (in μL to mL volumes) from the mixture vat and to dilute the sample to the 0.1 Bq range, prior to introducing the mixture into the Tension Metastable Fluid Detector systems for assessment and detection of the presence of specific key isotopes ($^{242}$Cm, $^{244}$Cm, $^{238}$Pu, $^{241}$Am and $^{239}$Pu). As explained earlier, the degree of dilution for alpha activity in the $10^{14}$ Bq/MTU and for fission activity in the $10^8$ Bq/MTU will necessarily be different. The second bank of detectors provides for a relatively exact (less than 1% error margin) estimate for the relative quantities of $^{239}$Pu and with greater error (approximately 10%) for $^{235}$U in the mixture for reasons explained earlier. These two types of detector banks can form the basic setup for various branches of the reprocessing stream. This is because the alpha-neutron producing dominant Cm isotopes are the last to be removed. At each intermediate stream, actinides are selectively isolated and additional detector banks or even active interrogation may be utilized (e.g., for monitoring for $^{235}$U which is a relatively weak alpha and neutron emitter).

The U/Tc extraction (UREX) line normally contains negligible quantities of transuranic isotopes. The U isotopes would primarily be $^{234}$U, $^{235}$U and $^{238}$U, and since $^{99}$Tc is a beta emitter with about a 0.2 million year half-life which TMFDs do not detect, the measurement is for only the three U isotopes. Due to extremely high Spontaneous Fission half-lives of over $10^{15}$y and consequently a very low level of fission activity, and also for alpha-emission half-lives of over $10^7$y in relation to the amount of uranium neutron production in this UREX extraction stream can be considered to be similar in intensity as background radiation. Such a UREX extraction line cannot be readily monitored for neutron activity via passive neutron detection unless unintentional diversion takes place for other actinide elements such as Pu. For such instances, the presence of significant neutron activity is a tell-tale sign and the two aforementioned TMFD bank types passively monitoring the UREX line would detect such an event. Active external neutron induced fission based monitoring does indeed offer such a possibility for active interrogation to decipher for $^{235}$U content. We have ascertained that either a 1 Ci Pu—Be isotope source or using an equivalent output of about $10^6$ n/s, 14 MeV D-T pulsed generator source neutrons can measure about 100 g quantities of U from fast neutron-induced fissions for determining the quantity of $^{238}$U and $^{235}$U within minutes of monitoring. The quantity of $^{235}$U in Spent Nuclear Fuels in this process stream can thus be determined in the mix but would require an external neutron source. In order to determine the quantity of $^{235}$U in Spent Nuclear Fuels a 1 Ci Pu—Be, equivalent $^{252}$Cf, or accelerator-driven sources can be used together with a down-scattering medium such as paraffin or polyethylene of about 10 mean free path lengths (e.g., 0.2 m) thickness. Such down-scattering is useful because the probability of fission (the cross-section) increases logarithmically with reduced neutron energy, rising to about 600 barns for $^{235}$U fission, versus only about 1 barn at 14 MeV levels. This can then be cross-checked using the sampling technique after dilution to provide direct information on alpha activities of $^{234}$U (4.77 MeV), $^{235}$U (4.58 MeV) and $^{238}$U (4.2 MeV) based upon the data shown in FIG. 4. The two independent checks of neutron and alpha radiation provide accurate monitoring of $^{235}$U content within 30 minutes to an hour. Sweeping the $P_{neg}$ tension pressures from about −9 bar to −10 bar (about 10% change) requires only the increase in rotational speed of the CTMFD system by about 3% since $P_{neg}$ levels vary quadratically with rotational speed and neutron output monitoring in the absence of active monitoring. This can be used to determine if material diversion is taking place since diversion of Cm/Pu/Am content even at about 0.1% would give rise to unmistakable signatures of neutron-alpha activity in the U/Tc stream because the $P_{neg}$ values required for detection of Cm/Pu/Am isotopes occurs at lower $P_{neg}$ values than that required for detecting U isotopes (FIGS. 4 and 7).

For a Cs—Sr extraction stream (FPEX) as shown in FIG. 1 with a mixture that presumably includes only beta-gamma emitters and no detectable neutron or alpha emitters, a single Tension Metastable Fluid Detector sensor having a sensitive volume in the range of about 300-500 cc, with an isopentane detector fluid, set to operate at $P_{neg}$ of around −5 bar can be used to reliably monitor for neutron activity above cosmic background levels. This can be used to provide an indication of the presence or absence of transuranic actinide (e.g., Pu) diversion. Alternatively, a two detector bank of TMFDs may also be utilized since the added cost and complexity with use of TMFDs is very low in comparison with known methods which require off-site shipment of liquid streams.

Background beta-gamma activity levels in the subsequent NPEX stream composed of Pu and Np elements, are significantly lower, for example about 1000-fold lower or less, and since Tension Metastable Fluid Detectors are already blind to beta-gamma radiation, the monitoring system would be the same as that described previously for the front end monitoring. A Tension Metastable Fluid Detector preferably having about 300-500 cc of detector fluid which is preferably isopentane at a $P_{neg}$ of about −6 bar could be used to monitor for neutrons. This can be coupled with a bank of 3 or more Tension Metastable Fluid Detectors (about 1 cc; acetone filled, $P_{neg}$ varying from −7 bar to about −9 bar) to simultaneously monitor for $^{238}$Pu, $^{239}$Pu, and $^{237}$Np). A similar embodiment could be used to monitor a TRUEX extraction stream comprising a balance of the transuranic elements or any similar set of TMFDs for neutron and alpha monitoring for $^{242}$Cm, $^{244}$Cm, and $^{241}$Am isotopes. This comprehensive monitoring system provides the advantage of allowing cross-checks in real-time with the measurements upfront to detect a diversion of Special Nuclear Materials.

While the above description is provided for monitoring of fissile isotopes such as $^{235}$U and $^{239}$Pu in extremely high gamma-beta fields for the UREX reprocessing scheme, the approach is general in nature and may be readily employed for selective neutron-alpha-fission activity monitoring, for other reprocessing schemes such as PuREX and for monitoring for storage and flow of SNMs within weapons manufacturing, deployment and stockpile facilities. In addition the detector systems have the ability to provide information about the direction from which the neutrons originate and also for imaging the sources and multiplicity as shown in FIG. 6 to identify what specific fissile isotope is present since fission of $^{235}$U releases about 2.5 neutrons/fission versus $^{252}$Cf which releases about 4 neutrons/fission. Therefore, the ATMFD technology may be deployed in numerous situations where neutron detection is needed and can be used to track the location and movement of fissile nuclei.

Table 4 summarizes the types of radiation that can be detected by the disclosed compositions and methods.

TABLE 4

Key Radiation Signatures Detectable by Tension Metastable Fluid Detector Systems

| Signature | Discussion |
| --- | --- |
| Alpha Energy Spectra (dissolved solutions) | U and Transuranic isotopes are intimately mixed in process solutions. The gamma blind Tension Metastable Fluid Detector is capable of discerning the presence of isotopes ranging from $^{238}$U to $^{239}$Pu to $^{242}$Cm. For deciphering isotopes in mixtures, convert the time vs. $P_{neg}$ information in FIG. 4 into quantitative measures of the actinide concentration in solutions using the radioactive rate constant additive principle. |
| Neutron Energy Spectra (~0.01 eV to 10 MeV energy) | Tension Metastable Fluid Detectors are capable of direct detection of thermal and fast neutrons (FIG. 6). This direct measurement is a remarkable improvement over current methods that use multiple thermal neutron detectors to infer spectral information. For reprocessing plants, the disclosed TMFDs could be used to scan (in minutes) the time vs. $P_{neg}$ information and thereby quantify an isotopic specific neutron spectrum. |
| Neutron Directionality (source location discernment) | A 10 cm diameter TMFD is able to detect and track an 8 kg $^{239}$Pu source within 30 s to within 10° with 80% confidence up to 25 m away. The disclosed TMFDs can be used to monitor, in virtual real-time, the flow of neutron-emitting Special Nuclear Materials within various piping streams of chemical processing plants. |
| Neutron Multiplicity (Direct Observation of Fission) | Fissile isotopes such as 235U and 239Pu may be detected using the active interrogation methods disclosed herein. In addition, neutron multiplicity data can be characterized. Existing systems rely on banks of multiple 3He detectors. ATMFD systems can decipher multiple coincident events within a single detector or a bank of detectors to decipher the isotope in question based on multiplicity. |
| Fission Product Recoil (Dissolved Fissile Actinides) | Fission fragments typically originate with energies ranging from 80 to 100 MeV on average. A TMFD using acetone as a detection fluid requires −7 to −9 bar to detect 1 to 5 MeV neutrons or alpha particles and only −0.2 bar to detect 80 to 100 MeV FFs, as shown in FIG. 7. This constitutes a signature for the presence of fissile materials. |

Figure 13:
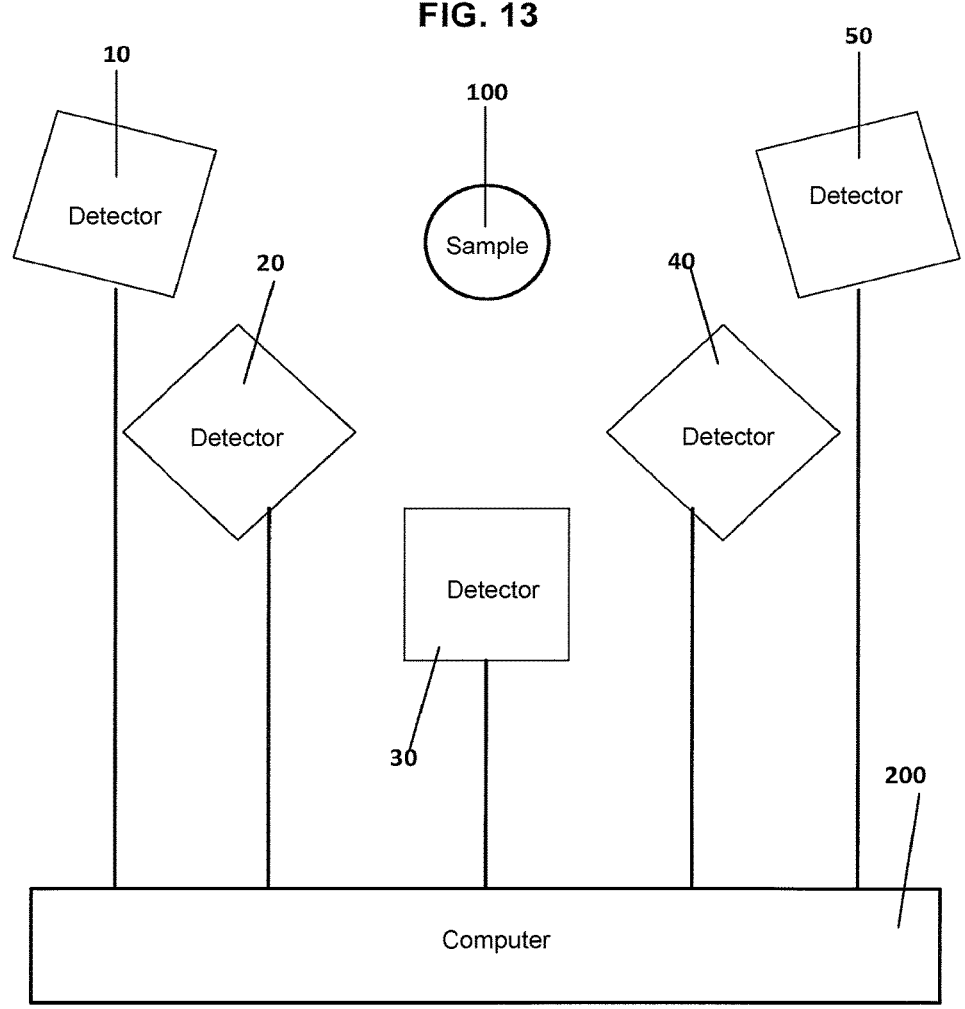
FIG. 13 provides an illustration of a detection system for detecting neutrons from a sample having five TMFD detectors set to distinct $P_{neg}$ values.

The neutron detection methods and system for neutron detection can be better understood with reference to FIGS. 7 and 13. FIG. 13 provides an illustration of a detection system for detecting neutrons from a sample 100. having five TMFD detectors 10, 20, 30, 40 and 50 that are set to distinct $P_{neg}$ values such that neutrons originating from different elements teat have different energies can be distinguished. For example, if detection of neutrons from each of $^{238}$U, $^{234}$U, $^{239}$Pu, $^{241}$Am, $^{238}$Pu, $^{244}$Cm, and fission events are desired, detector 10, for example, could be set with a Pneg of −10 bar according to FIG. 7. To detect $^{234}$U, $^{239}$Pu, $^{241}$Am, $^{238}$Pu, $^{244}$Cm, and fission events, detector 20 could be set to have a $P_{neg}$ of greater than −9.5 bar and less than −9 bar. To detect $^{239}$Pu, $^{241}$Am, $^{238}$Pu, $^{244}$Cm, and fission events, detector 30 could be set to have a $P_{neg}$ of greater than −9.0 bar and less than −8.5 bar. To detect $^{241}$Am, $^{238}$Pu, $^{244}$Cm, and fission events, detector 40 could be set to have a $P_{neg}$ of greater than −8.5 bar and less than −8.1 bar. To detect $^{234}$U, $^{239}$Pu, $^{241}$Am, $^{238}$Pu, $^{244}$Cm, and fission events, detector 20 could be set to have a $P_{neg}$ of greater than −9.5 bar and less than −9 bar. To detect $^{244}$Cm, and fission events, detector 50 could be set to have a $P_{neg}$ of greater than −8.0 bar and less than −7 bar. A detector could also be set to have a Pneg of between about −0.2 and −7 bar for detection of $^{235}$U fission. The detectors can communicate with a computer 200 that can be used to calculate the amounts of various neutron sources present in sample 100. The computer can also be implemented with ORIGEN code and used to carry out the calculations of actinide species present in spent nuclear fuel.

The invention claimed is:

1. A method for monitoring actinides during reprocessing of spent nuclear fuel after 30-year cool down comprising:
enriching a spent nuclear fuel sample derived from burned nuclear fuel having a specific initial enrichment,
estimating the amount of actinides in the sample,
determining actinide masses and spent fuel neutron production from fission and a, n production,
predicting fission and a activity of actinides using estimated masses and T½,
measuring neutron production with a TMFD,
comparing measured neutron and fission production with predicted neutron and fission production
repeating the predicting step until the numbers agree within about 10% or less of the measured neutron production,
removing a sample from the dissolved fuel,
diluting the sample to about 0.1 to about 10 decay per second to allow detection in the TMFD system within about 5 to about 60 seconds,
estimating the radiation activity of the sample,
confirming absence of $^{242}$Cm activity,
measuring $^{244}$Cm and determining the concentration of $^{244}$Cm in the sample measuring the combined $^{238}$Pu, $^{241}$Am, and $^{244}$Cm and determining the concentration of $^{283}$Pu, $^{241}$Am in the sample,
re-calibrating the actinide concentration estimates to correspond with measured amounts of Cm, Am, and Pu within about 10% or less,
determining the concentrations of $^{239}$Pu from $^{241}$Am, $^{238}$Pu, $^{244}$Cm and estimated ratios,
cross verifying the amounts of $^{239}$Pu from extraction stream using active TMFD measurement.

2. A method for monitoring actinides during reprocessing of spent nuclear fuel after 180-day cool down comprising:
enriching a spent nuclear fuel sample,
estimating the amount actinides in the sample,
determining actinide masses and spent fuel neutron production from fission and α, n production,
predicting fission and α activity of actinides using estimated masses and T½,
measuring neutron production with a calibrated TMFD,
comparing measured neutron and fission production with predicted neutron and fission production,
if the measured and predicted neutron production numbers do not agree repeat the predicting step until the numbers agree within 10%,
removing a sample from the dissolved fuel,
diluting the sample to about 0.1 to about 10 decay per second to allow detection in the TMFD system within about 5 to about 60 seconds,
estimating the radiation activity of the sample,
measuring $^{242}$Cm and determining the concentration of $^{242}$Cm in the sample,
measuring combined $^{244}$Cm and $^{242}$Cm and determining the concentration of $^{244}$Cm in the sample,
measuring the combined $^{238}$Pu, $^{242}$Cm, and $^{244}$Cm and determining the concentration of $^{238}$Pu, in the sample,
measuring combined 238Pu, $^{241}$Am, $^{244}$Cm and $^{242}$Cm and determining the concentration of $^{241}$Am in the sample,
re-calibrating the actinide concentration estimates for consistency with measured amounts of Cm, Am, and Pu,
determining $^{239}$Pu from $^{238}$Pu, $^{241}$Am, $^{244}$Cm and $^{242}$Cm measurement and estimated ratios,
cross-verifying the amounts of $^{239}$Pu by either active TMFD monitoring or TMFD sipping based monitoring of $^{238}$Pu and $^{239}$Pu.

* * * * *